(12) United States Patent
Ma

(10) Patent No.: US 10,045,981 B2
(45) Date of Patent: Aug. 14, 2018

(54) SELECTIVE KINASE INHIBITORS

(71) Applicant: JAKPHARM, LLC, Woodbridge, CT (US)

(72) Inventor: Haiching Ma, Malvern, PA (US)

(73) Assignee: JAKPharm, LLC, Woodbridge, CT (US)

(*) Notice: Subject to any disclaimer, the term of this patent is extended or adjusted under 35 U.S.C. 154(b) by 0 days.

(21) Appl. No.: 15/360,198

(22) Filed: Nov. 23, 2016

(65) Prior Publication Data

US 2017/0143706 A1 May 25, 2017

Related U.S. Application Data

(60) Provisional application No. 62/259,631, filed on Nov. 24, 2015.

(51) Int. Cl.
  *C07D 241/42* (2006.01)
  *C07D 403/10* (2006.01)
  *A61K 31/498* (2006.01)

(52) U.S. Cl.
  CPC .......... *A61K 31/498* (2013.01); *C07D 241/42* (2013.01); *C07D 403/10* (2013.01)

(58) Field of Classification Search
  CPC .............................. C07D 241/42; C07D 403/10
  See application file for complete search history.

(56) References Cited

U.S. PATENT DOCUMENTS

| | | | |
|---|---|---|---|
| 5,932,580 A | 8/1999 | Levitzki et al. | |
| 5,981,569 A | 11/1999 | App et al. | |
| 6,177,433 B1 | 1/2001 | Uckun et al. | |
| 6,627,754 B2 | 9/2003 | Blumenkopf et al. | |
| 7,084,147 B2 | 8/2006 | Cockerill et al. | |
| 7,091,208 B2 | 8/2006 | Blumenkopf et al. | |
| 7,112,594 B2 | 9/2006 | Ushio et al. | |
| 7,122,552 B2 | 10/2006 | Ledford | |
| 7,129,253 B2 | 10/2006 | Glennon et al. | |
| 7,189,734 B2 | 3/2007 | Cockerill et al. | |
| 7,192,963 B2 | 3/2007 | Blumenkopf et al. | |
| 7,244,735 B2 | 7/2007 | Straub et al. | |
| 7,262,200 B2 | 8/2007 | Aronov et al. | |
| 7,335,667 B2 | 2/2008 | Rodgers et al. | |
| 7,396,832 B2 | 7/2008 | Lindsley et al. | |
| 7,432,370 B2 | 10/2008 | Wilcox et al. | |
| 7,435,814 B2 | 10/2008 | Singh et al. | |
| 7,435,879 B2 | 10/2008 | Streit et al. | |
| 8,592,415 B2 | 11/2013 | Ma et al. | |
| 2005/0113395 A1 | 5/2005 | Changelian | |
| 2006/0069071 A1 | 3/2006 | Geracioti | |
| 2006/0183761 A1 | 8/2006 | Ledeboer et al. | |
| 2007/0004762 A9 | 1/2007 | Ledeboer et al. | |
| 2008/0009488 A1 | 1/2008 | Anand et al. | |
| 2011/0166129 A1 | 7/2011 | Machacek et al. | |

FOREIGN PATENT DOCUMENTS

| | | |
|---|---|---|
| CN | 1966500 | 5/2007 |
| DE | 281380 A5 | 8/1990 |
| JP | S56-90067 | 7/1981 |
| JP | 2000-309578 A | 11/2000 |
| JP | 2002-534512 A | 10/2002 |
| JP | 2004-525961 A | 8/2004 |
| JP | 2005-530726 A | 10/2005 |
| JP | 2005-533010 A | 11/2005 |
| JP | 2007-536224 A | 12/2007 |
| JP | 2008-506778 A | 3/2008 |
| JP | 2008-530111 A | 8/2008 |
| JP | 2009-096804 A | 5/2009 |
| JP | 2009-196973 A | 9/2009 |
| JP | 2011-519863 A | 7/2011 |
| WO | 1998/05335 | 2/1998 |
| WO | 1999/42463 | 8/1999 |
| WO | 1999/065909 | 12/1999 |
| WO | 2000/000202 | 1/2000 |
| WO | 2002/000196 A2 | 1/2002 |
| WO | 2003/007959 A1 | 1/2003 |
| WO | 2003/062234 A1 | 7/2003 |
| WO | 2004/099205 A1 | 11/2004 |
| WO | 2005/056547 A2 | 6/2005 |
| WO | 2006053227 A2 | 5/2006 |
| WO | 2006/069080 A2 | 6/2006 |
| WO | 2006/078283 A2 | 7/2006 |
| WO | 2006/079478 A2 | 8/2006 |
| WO | 2007/053452 A1 | 5/2007 |
| WO | 2007/089768 A2 | 8/2007 |
| WO | 2008/047831 A1 | 4/2008 |

(Continued)

OTHER PUBLICATIONS

Readinger, et al., "Selective targeting of ITK blocks multiple steps of HIV replication," PNAS (May 6, 2008), 105 (18):6684-6689.
Säemann, et al., "Prevention of CD40-Triggered Dendritic Cell Maturation and Induction of T-Cell Hyporeactivity by Targeting of Janus Kinase 3," Am J Transplant (2003), 3:1341-1349.
Scott, et al., "Jaks, STATs, Cytokines, and Sepsis," Clin. Diagn. Lab. Immunol. (Nov. 2002), 9(6):1153-1159.
Sills, et al., "In Vitro and In Vivo Characterization of a Novel JAK3 Tyrosine Kinase Inhibitor," Inflammation Res. Assoc. Fourteenth International Conference (Oct. 15-19, 2006), Hyatt Regency Chesapeake Bay, Cambridge, Maryland, Poster A155.
Smits et al., Fragment based Design of new H4 receptor-ligands with Anti-inflammatory Properties In Vivo (2008) J. Med. Chem. 43(1):2457-2467.
Steinman, et al., "Immune Therapy for Autoimmune Diseases," Science (Jul. 9, 2004), 305:212-216.

(Continued)

*Primary Examiner* — Brian E McDowell
(74) *Attorney, Agent, or Firm* — Pepper Hamilton LLP

(57) ABSTRACT

The present disclosure relates to methods of modulating (for example, inhibiting) activity of JAK3, comprising contacting the JAK3 with a compound of Formula I or pharmaceutically acceptable salt thereof, wherein constituent members are provided hereinwith. The present disclosure further provides novel compounds and compositions as well as their methods of preparation and use. The disclosed JAK3 inhibitors may be used in the treatment of JAK3-associated diseases including, for example, inflammatory and autoimmune disorders.

6 Claims, 4 Drawing Sheets

(56) References Cited

FOREIGN PATENT DOCUMENTS

| WO | 2008/057058 | A1 | 5/2008 |
|---|---|---|---|
| WO | 2008/118454 | A2 | 10/2008 |
| WO | 2008/118468 | A1 | 10/2008 |
| WO | 2008/141065 | A1 | 11/2008 |
| WO | 2008/148867 | A2 | 12/2008 |
| WO | 2010/023924 | A1 | 3/2010 |
| WO | 2010042225 | A2 | 4/2010 |
| WO | 2017/091681 | | 6/2017 |

OTHER PUBLICATIONS

Supplementary European Search Report dated Jun. 6, 2012 for corresponding EP Appl. 10741733.
Suzuki, et al., "Janus kinase 3 (Jak3) is essential for common cytokine receptor γ chain (γc)-dependent signaling: comparative analysis of γc, Jak3 and γc and Jak3 double-deficient mice," International Immunology (2000), 12 (2):123-132.
Thomis, et al., "The role of Jak3 in lymphoid development, activation, and signaling," Current Opinion in Immunology (1997), 9:541-547.
Thomis, et al., "Defects in B Lymphocyte Maturation and T Lymphocyte Activation in Mice Lacking Jak3," Science (Nov. 3, 1995), 270:794-797.
Tibbles, Role of a JAK3-dependent Biochemical Signaling Pathway in Platelet Activation and Aggregation, J. Biol. Chem. (May 25, 2001), 276(21):17815-17822.
Trieu, et al., "A Specific Inhibitor of Janus Kinase-3 Increases Survival in a Transgenic Mouse Model of Amyotrophic Lateral Sclerosis," Biochem. Biophys. Res. Comm. (2000), 267(1):22-25.
Verbsky, et al., "Expression of Janus Kinase 3 in Human Endothelial and Other Non-lymphoid and Non-myeloid Cells," J. Biol. Chem. (Jun. 14, 1996), 271(24):13976-13980.
Walters, et al., "Activating alleles of JAK3 in acute megakaryoblastic leukemia," Cancer Cell (Jul. 2006), 10:65-75.
Wang et al., "Synthesis and Evaluation of Benzothiazole-Based Analogues as Novel, Potent, and Selective Fatty Acid Amide Hydrolase Inhibitors," J. of Med. Chem., (Jan. 8, 2009), 52(1):170-180.
Wuts, et al., "The Role of Protective Groups in Organic Synthesis," in Greene's Protective Groups in Organic Synthesis, John Wiley & Sons, Inc., 4th Ed. (2007), 1-15.
Zhong, et al., "Stat3 and Stat4: Members of the family of signal transducers and activators of transcription," Proc. Natl. Acad. Sci. USA (May 1994), 91:4806-4810.
Abrams et al., "A Clonal CD4-Positive T-Cell Line Established from the Blood of a Patient with Sézary Syndrome," J Investig Dermatol (Jan. 1991), 96(1):31-37.
Benekli, et al., "Signal transducer and activator of transcription proteins in leukemias," Blood (Apr. 15, 2003), 101 (8):2940-2954.
Berge, et al., "Pharmaceutical Salts," The Journal of Pharmaceutical Sciences (Jan. 1977), 66(1):1-19.
Borie, et al., "Immunosuppression by the JAK3 Inhibitor CP-690,550 Delays Rejection and Significantly Prolongs Kidney Allograft Survival in Nonhuman Primates," Transplantation (Apr. 15, 2005), 79(7):791-801.
Borie, et al., "JAK3 inhibition, a viable new modality of immunosuppression for solid organ transplants," Trends Mol. Med. (Oct. 12, 2004), 10(11):532-541.
Buckley, et al., "Human severe combined immunodeficiency: Genetic, phenotypic, and functional diversity in one hundred eight infants," J Pediatr (Mar. 1997), 130(3):378-387.
Cetkovic-Cvrlje, et al., "Targeting JAK3 with JANEX-1 for prevention of autoimmune type 1 diabetes in NOD mice," Clinical Immunology (2003), 106:213-225.
Cetkovic-Cvrlje, et al., "Therapeutic Potential of Janus Kinase 3 (JAK3) Inhibitors," Current Pharmaceutical Design (2004), 10(15):1767-1784.
Changelian, et al., "The specificity of JAK3 kinase inhibitors," Blood (Dec. 19, 2007), 111(4):2155-2157.
Changelian, et al., "Prevention of Organ Allograft Rejection by a Specific Janus Kinase 3 Inhibitor," Science (Oct. 31, 2003), 302:875-878.
Conklyn, et al., "The JAK3 inhibitor CP-690550 selectively reduces NK and CD8+ cell numbers in cynomolgus monkey blood following chronic oral dosing," Journal of Leukocyte Biology (Dec. 2004), 76:1248-1255.
Corona et al., Systhesis of N-(5,7-diamino-3-phenyl-quinoxalin-2-yl)-3,4,5-substituted anilines and N-[4[(5,7-diamino-3-phenylquinoxalin-2-yl)amino]benzoyl]-L-glutamic acid diethyl ester: Evaluation of in vitro anti-cancer and anti-folate activities, Euro. J. Med. Chem. (2008) 43(1):189-203.
Darnell, et al., "Jak-STAT Pathways and Transcriptional Activation in Response to IFNs and Other Extracellular Signaling Proteins," Science (Jun. 3, 1994), 264(15640:1415-1421.
Database Abstract, Compound with Registry No. 692732-77-7, Retrieved from online database Jun. 14, 2004, XP-002677239.
Database Abstract, Compound with Registry No. 697238-78-1, Retrieved from online database Jun. 22, 2004, XP002677240.
Database Abstract, Compound with Registry No. 832679-46-6, Retrieved from online database Feb. 17, 2005, XP002677241.
Database Abstract, Compound with Registry No. 866131-45-5, Retrieved from online database Oct. 26, 2005, XP002677242.
Demoulin, et al., "A Single Tyrosine of the Interleukin-9 (IL-9) Receptor Is Required for STAT Activation, Antiapoptotic Activity, and Growth Regulation by IL-9," Mol. Cell. Biol. (Sep. 1996), 16(9):4710-4716.
Deuse, et al., "Novel Immunosuppression: R348, a JAK3- and Syk-Inhibitor Attenuates Acute Cardiac Allograft Rejection," Transplantation (Mar. 27, 2008), 85(6):885-892.
Fedorov, et al., "A systematic interaction map of validated kinase inhibitors with Ser/Thr kinases," PNAS (Dec. 18, 2007), 104(51):20523-20528.
Ihle, et al., Jaks and Stats in signaling by the cytokine receptor superfamily, TIG (Feb. 1995), 11(2):69-74.
Ihle, "Janus kinases in cytokine signalling," Phil. Trans. R.. Soc. Lond. B (1996), 351:159-166.
International Search Report and Written Opinion in Appl. No. PCT/US2010/023924 dated Apr. 1, 2010.
International Search Report and Written Opinion in Appl. No. PCT/US2016/063515 dated Feb. 2, 2017.
Johnston, et al., "Phosphorylation and activation of the Jak-3 Janus kinase in response to interleukin-2," Nature (Jul. 14, 1994), 370:151-15.3.
Jurlander, et al., "Characterization of Interleukin-10 Receptor Expression on B-Cell Chronic Lymphocytic Leukemia Cells," Blood (Jun. 1, 1997), 89(11):4146-4152.
Kaneko, et al., "Rescue by cytokines of apoptotic cell death induced by IL-2 deprivation of human antigen-specific T cell clones," Clin. Exp. Immun. (Jul. 1997) 109:185-193.
Karaman, et al., "A quantitative analysis of kinase inhibitor selectivity," Nature Biotech. (Jan. 8, 2008), 26 (1):127-132.
Kiyoi, et al., "JAK3 mutations occur in acute megakaryoblastic leukemia both in Down syndrome children and non-Down syndrome adults," Leukemia (Jan. 25, 2007), 21:574-576.
Leonard, "STATs and cytokine specificity," Nature Medicine (Sep. 1996), 2(9):968-969.
Levy, "The House that JAK/STAT Built," Cytokine & Growth Factor Reviews (1997), 8(1):81-90.
Lin, et al. "Constitutive Activation of JAK3/STAT3 in Colon Carcinoma Tumors and Cell Lines," AJP (Oct. 2005), 167(4):969-980.
Lin, et al. "Selective Itk Inhibitors Block T-Cell Activation and Murine Lung Inflammation," BioChemistry (2004), 43:11056-11062.
Luo, et al., "Inhibitors of JAKs/STATs and the kinases: a possible new cluster of drugs," DDT (Mar. 2004), 9 (6):268-275.
Ma, et al., "The challenge of selecting protein kinase assays for lead discovery optimization," Expert Opin Drug Discov. (Jun. 2008), 3(6):607-621.
Macchi, et al., "Mutations of Jak-3 gene in patients with autosomal severe combined immune deficiency (SCID)," Nature (Sep. 7, 1995), 377:65-68.

(56) References Cited

OTHER PUBLICATIONS

Malaviya, et. al., "Targeting Janus Kinase 3 in Mast Cells Prevents Immediate Hypersensitivity Reactions and Anaphylaxis," Journal of Biological Chemistry (Sep. 17, 1999), 274(38):27028-27038.

Marzec, et al., "Inhibition of ALK enzymatic activity in T-cell lymphoma cells induces apoptosis and suppresses proliferation and STAT3 phosphorylation independently of Jak3," Laboratory Investigation (Sep. 19, 2005) 85:1544-1554.

Milici, et al., "Cartilage preservation by inhibition of Janus kinase 3 in two rodent models of rheumatoid arthritis," Arthritis Research & Therapy (Jan. 30, 2008), 10:R14.

Mosmann, "Rapid Colorimetric Assay for Cellular Growth and Survival: Application to Proliferation and Cytotoxicity Assays," J. Immunol. Methods (1983), 65:55-63.

Nakamura, et al., "An Epidermal Growth Factor Receptor/Jak2 Tyrosine Kinase Domain Chimera Induces Tyrosine Phosphorylation of Stat5 and Transduces a Growth Signal in Hematopoietic Cells," J. Biol. Chem. (Aug. 9, 1996), 271(32):19483-19488.

Nosaka, et al., "Defective Lymphoid Development in Mice Lacking Jak3," Science (Nov. 3, 1995), 270 (5237):800-802.

Notarangelo, et al., "Of genes and phenotypes: the immunological and molecular spectrum of combined immune deficiency. Defects of the γc-JAK3 signaling pathway as a model," Immunological Reviews (2000), 178:39-48.

Olive, "Quantitative methods for the analysis of protein phosphorylation in drug development," Expert Rev. Proteomics (2004), 1(3):327-341.

O'Shea, et al., "New strategies for immunosuppression: interfering with cytokines by targeting the Jak/Stat pathway," Current Opinion in Rheumatology (2005), 17:305-311.

O'Shea, et al., "Cytokine Signaling Modules in Inflammatory Responses," Immunity (Apr. 2008), 28:477-487.

O'Shea, et al., "Cytokines and Autoimmunity," Nature Reviews (Jan. 2002), 2:37-45.

Papageorgiou, et al., "Is JAK3 a new drug target for immunomodulation-based therapies?," TRENDS in Pharmacological Sciences (Sep. 24, 2004), 25(11): 558-562.

Pesu, et al., Therapeutic targeting of Janus kinases, Immunol Rev. (Jun. 2008), 223:132-142.

Ravin, "Preformulation, Remington's Pharmaceutical Science," 17th ed., Mack Publishing Company, Easton, PA (1985), 1409-1423.

SELECTIVE KINASE INHIBITORS

CROSS-REFERENCE TO RELATED APPLICATIONS

This application claims priority to U.S. Provisional Patent Application Ser. No. 62/259,631 entitled SELECTIVE KINASE INHIBITORS, filed on Nov. 24, 2015, which is hereby incorporated by reference in its entirety.

BRIEF SUMMARY

This disclosure relates to compounds, pharmaceutically acceptable salts thereof, and compositions thereof, methods of preparation of the same, as well as methods of use for inhibition of JAK3 and/or treatment of JAK3-associated diseases. The methods, compounds, and compositions disclosed herein relate to compounds useful for modulating (for example, inhibiting) activity of Janus Kinase-3 (JAK3) and/or treating JAK3-associated diseases, disorders or conditions including, for example, those involving the immune system, autoimmune diseases, an allergic or type I hypersensitivity reactions, hair-loss disorders, and skin disorders.

New or improved agents which specifically inhibit JAK3 are continually needed for developing new and more effective pharmaceuticals to treat JAK3-associated diseases, disorders, and conditions. The compounds, compositions and methods described herein are directed toward these needs and other ends.

Some embodiments provide for JAK3 inhibitor compounds selected from:

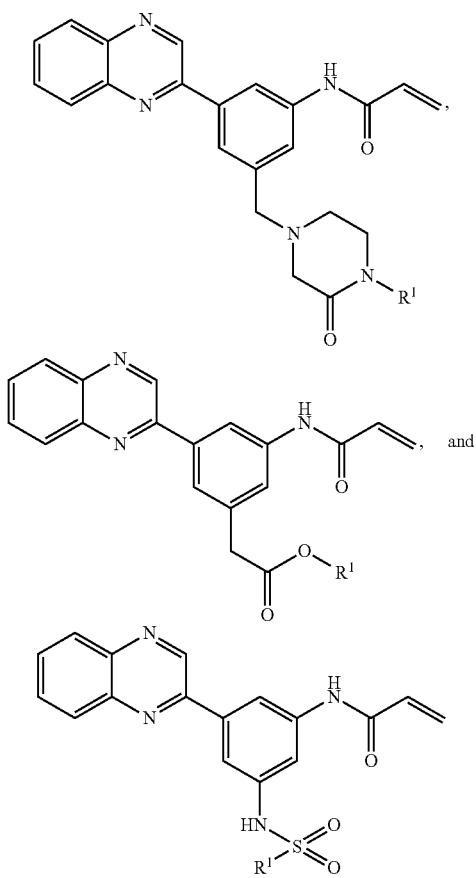

wherein $R^1$ is H or $C_1$-$C_6$ alkyl;
or pharmaceutically acceptable salt thereof.

In some embodiments, the JAK3 inhibitor compound is

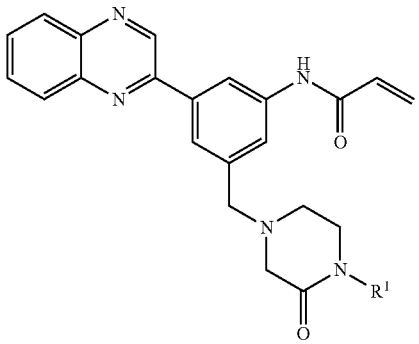

wherein $R^1$ is H or $C_1$-$C_6$ alkyl;
or pharmaceutically acceptable salt thereof.

In some embodiments, the JAK3 inhibitor compound is

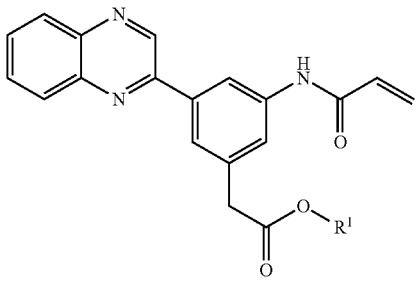

wherein $R^1$ is H or $C_1$-$C_6$ alkyl;
or pharmaceutically acceptable salt thereof.

In some embodiments, the JAK3 inhibitor compound is

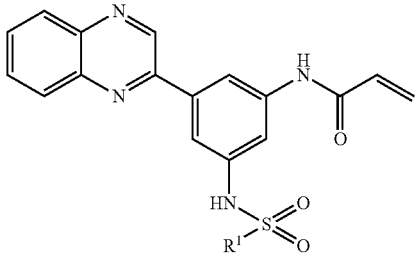

wherein $R^1$ is H or $C_1$-$C_6$ alkyl;
or pharmaceutically acceptable salt thereof.

In some embodiments, the JAK3 inhibitor compound is a compound of formula 1a:

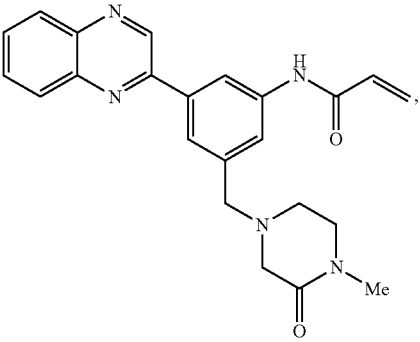

or pharmaceutically acceptable salt thereof.

In some embodiments, the JAK3 inhibitor compound is a compound of formula 1b:

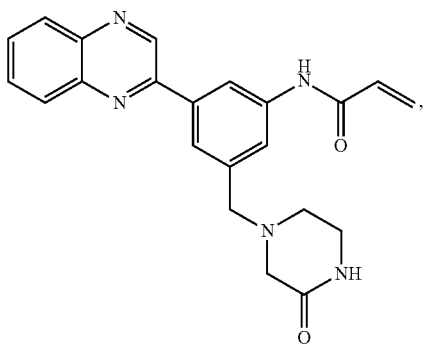

or pharmaceutically acceptable salt thereof.

Some embodiments provide a method of inhibiting an activity of JAK3 comprising contacting said JAK3 with a JAK3 inhibitor compound selected from:

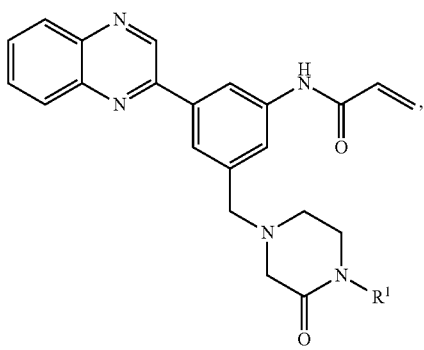

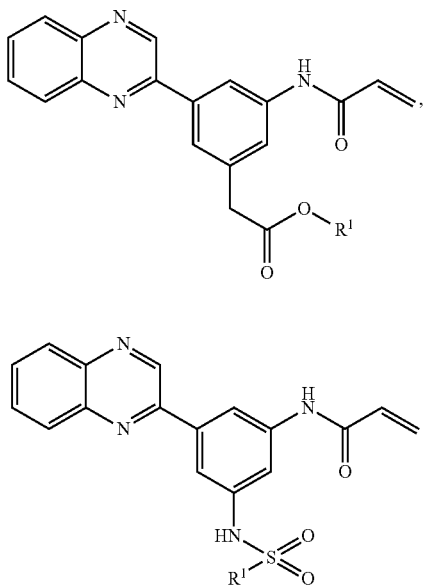

wherein $R^1$ is H or $C_1$-$C_6$ alkyl;

or pharmaceutically acceptable salt thereof.

In some embodiments of the method, the JAK3 inhibitor compound is

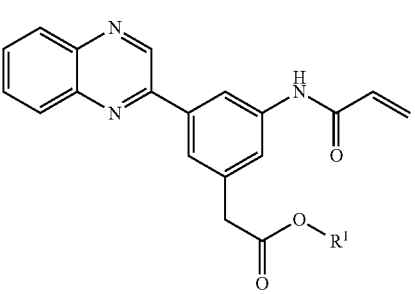

wherein $R^1$ is H or $C_1$-$C_6$ alkyl;

or pharmaceutically acceptable salt thereof.

In some embodiments of the method, the JAK3 inhibitor compound is

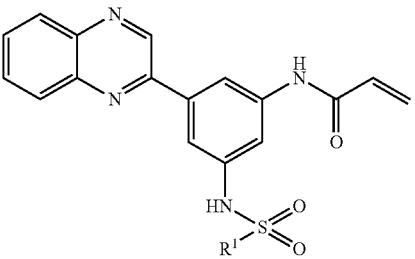

wherein $R^1$ is H or $C_1$-$C_6$ alkyl;

or pharmaceutically acceptable salt thereof.

Some embodiments provide for a method of treating a JAK3-associated condition, disease, or disorder in a patient comprising administering to said patient a therapeutically effective amount of a JAK3 inhibitor compound selected from:

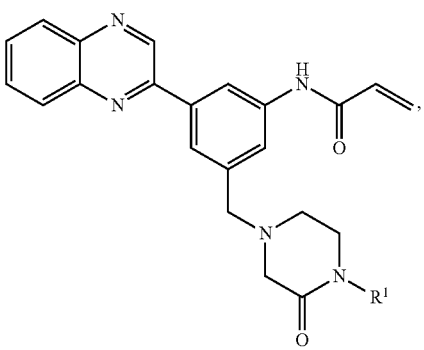

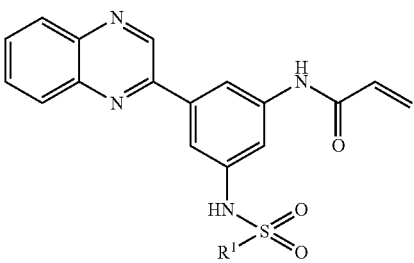

wherein R¹ is H or $C_1$-$C_6$ alkyl;
or pharmaceutically acceptable salt thereof.

In some embodiments of the method, the JAK3 inhibitor compound is wherein R¹ is H or $C_1$-$C_6$ alkyl;
or pharmaceutically acceptable salt thereof.

In some embodiments of the method, the JAK3 inhibitor compound is wherein R¹ is H or $C_1$-$C_6$ alkyl;
or pharmaceutically acceptable salt thereof.

In some embodiments of the method, the JAK3-associated disease, disorder or condition is selected from one involving the immune system, an autoimmune disease, an allergic or type I hypersensitivity reaction, a hair-loss disorder, and a skin disorder.

In some embodiments of the method, the JAK3-associated disease, disorder, or condition is one involving the immune system, selected from organ transplant rejection, allograft rejection, and graft versus host disease (GVHD), mast cell mediated immediate hypersensitivity reaction, platelet aggregation, and thrombus formation.

In some embodiments of the method, the JAK3-associated disease, disorder, or condition is an autoimmune disease selected from multiple sclerosis, rheumatoid arthritis, juvenile arthritis, psoriatic arthritis, type I diabetes, lupus, including systemic lupus, erythematosus, chronic cutaneous lupus, discoid lupus, tumid lupus, lupus profundus, subacute cutaneous lupus erythematosus, neonatal lupus, drug-induced lupus, and local or generalized acute cutaneous lupus, psoriasis, inflammatory bowel disease, ulcerative colitis, Crohn's disease, ankylosing spondylitis, myasthenia gravis, immunoglobulin nephropathies, autoimmune thyroid disorders, an autoimmune bullous skin disorder, pemphigus vulgaris (PV), bullous pemphigoid (BP), and rheumatoid arthritis.

In some embodiments of the method, the JAK3-associated disease, disorder, or condition is an allergic or type I hypersensitivity reaction selected from urticarial, eczema, conjunctivitis, rhinorrhea, rhinitis, asthma, gastroenteritis, familial amyotrophic lateral sclerosis, lupus, including systemic lupus, erythematosus, chronic cutaneous lupus, discoid lupus, tumid lupus, lupus profundus, subacute cutaneous lupus erythematosus, neonatal lupus, drug-induced lupus, and local or generalized acute cutaneous lupus, multiple sclerosis, Type I diabetes and complications from diabetes, cancer, asthma, rhinitis, atopic dermatitis, autoimmune thyroid disorders, Alzheimer's disease, leukemia, and thrombus.

In some embodiments of the method, the JAK3-associated disease, disorder, or condition is a skin disorder selected from vitiligo, localized vitiligo, focal vitiligo, generalized vitiligo, segmental vitiligo, acral vitiligo, facial vitiligo, acrofacial vitiligo, mucosal vitiligo, confetti vitiligo, trichrome vitiligo, marginal inflammatory vitiligo, quadrichrome vitiligo, blue vitiligo, Koebner phenomenon, vulgaris vitiligo, mixed acrofacial and vulgaris vitiligo, universal vitiligo, psoriasis, psoriasis vulgaris, atopic dermatitis, alopecia areata, patchy alopecia areata, alopecia totalis, alopecia universalis, ophiasis pattern alopecia areata, sisaihpo pattern alopecia areata, androgenetic alopecia (male and female pattern hair loss), telogen effluvium, hypotrichosis, hereditary hypotrichosis simplex, scarring alopecia, lichen planopilaris, central centrifugal cicatricial alopecia, skin rash, skin irritation, skin sensitization, contact dermatitis, and allergic contact dermatitis.

In some embodiments of the method, the JAK3-associated disease, disorder, or condition is a hair loss disorder selected from alopecia areata, androgenetic alopecia (male and female pattern hair loss), lichen planopilaris, telogen effluvium, tinea capitis, hypotrichosis, and hereditary hypotrichosis simplex.

Some embodiments further provide novel compounds and novel pharmaceutical compositions comprising the same and at least one pharmaceutically acceptable carrier.

Some embodiments further provide methods of use and preparation of the novel compounds and pharmaceutical compositions provided herein.

DETAILED DESCRIPTION

Figure 1:
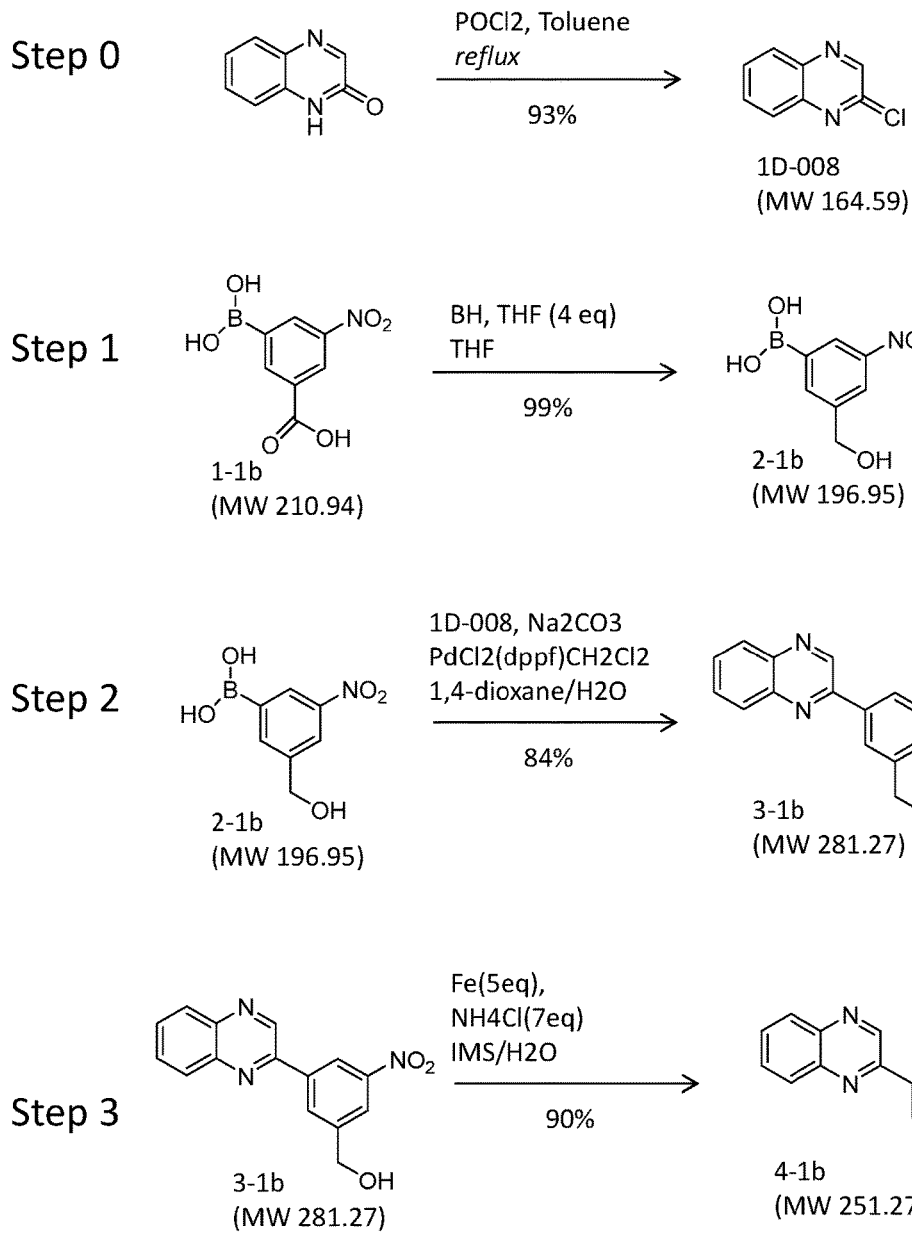
FIG. 1 depicts a reaction scheme in accordance with one embodiment disclosed herein.
Figure 1:
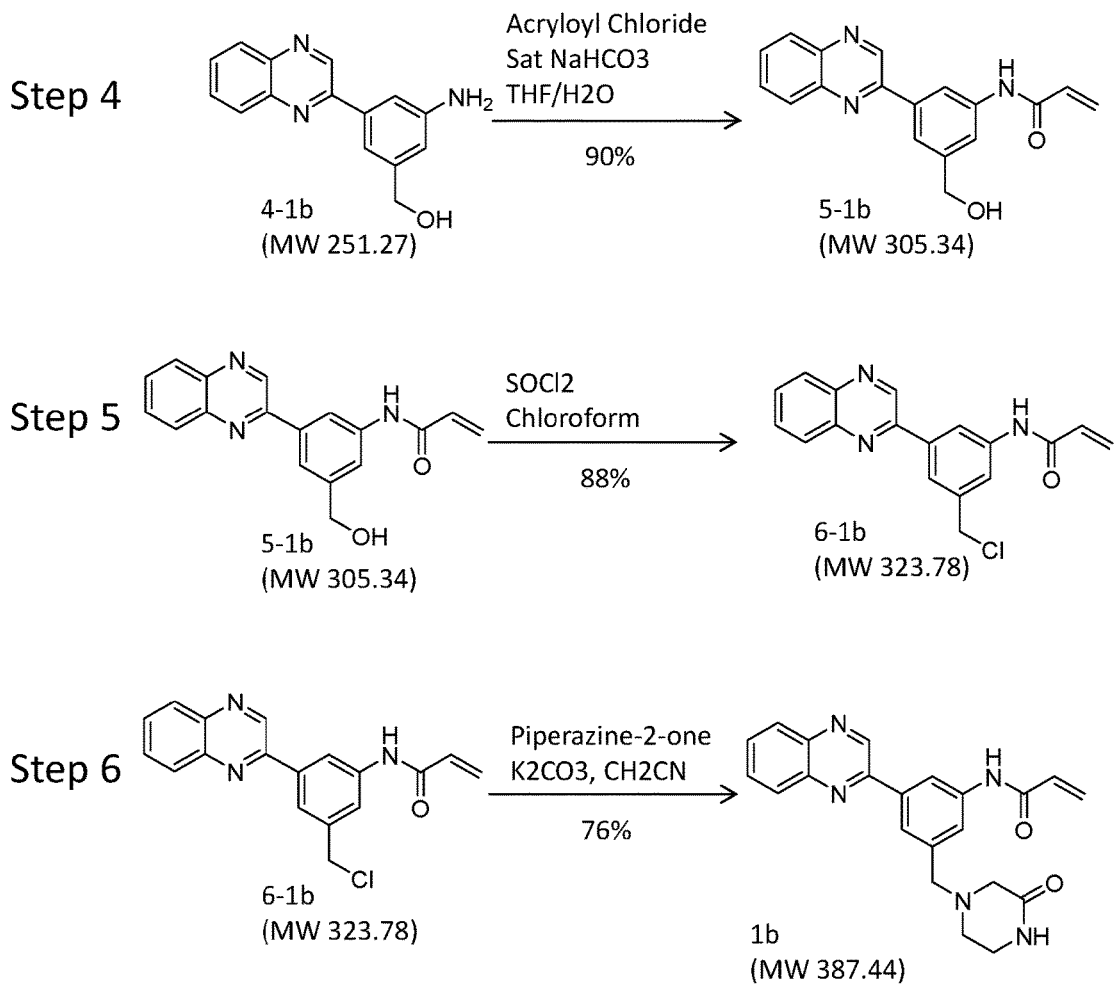

Disclosed herein are JAK3 modulating compounds, pharmaceutically acceptable salts thereof, compositions containing them, method of making them and methods of using them.

The compounds described herein have been shown to be selective JAK3 inhibitors. The JAK3 inhibitor compounds include

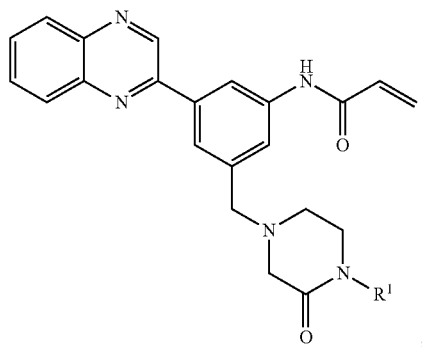

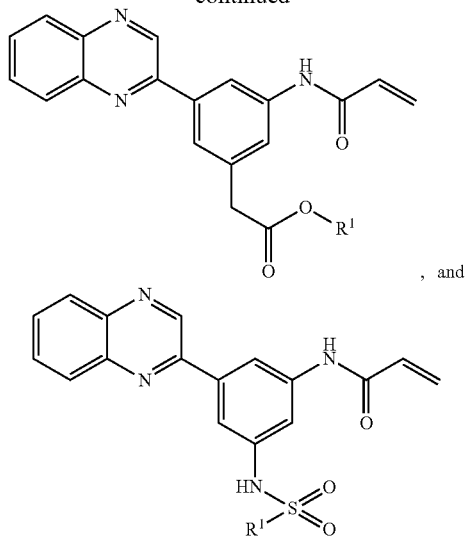

wherein $R^1$ is H or $C_1$-$C_6$ alkyl; or pharmaceutically acceptable salt thereof.

In some embodiments, the JAK3 inhibitor compound is

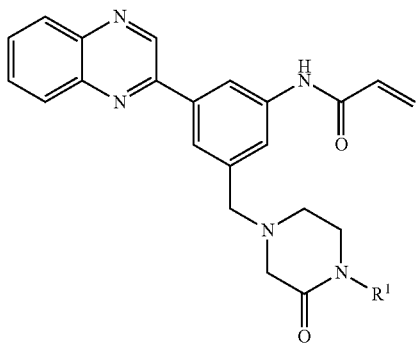

wherein $R^1$ is H or $C_1$-$C_6$ alkyl; or pharmaceutically acceptable salt thereof.

In some embodiments, the JAK3 inhibitor compound is a compound of formula 1a:

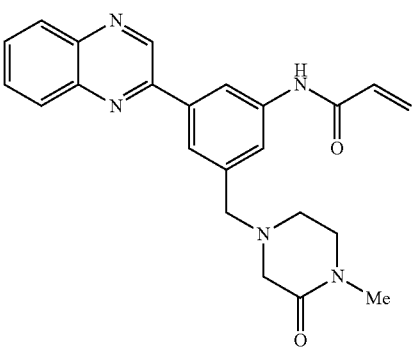

or pharmaceutically acceptable salt thereof.

In some embodiments, the JAK3 inhibitor compound is a compound of formula 1b:

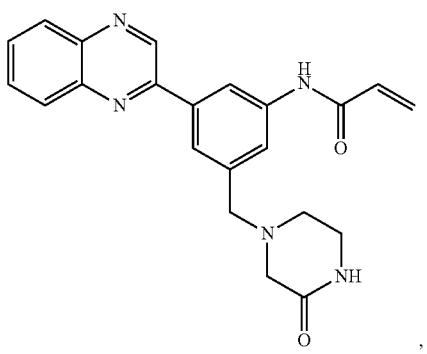 [SMILES: C=CC(=O)Nc1cc(CN2CCNC(=O)C2)cc(-c2cnc3ccccc3n2)c1]

or pharmaceutically acceptable salt thereof.

In some embodiments, the JAK3 inhibitor compound is

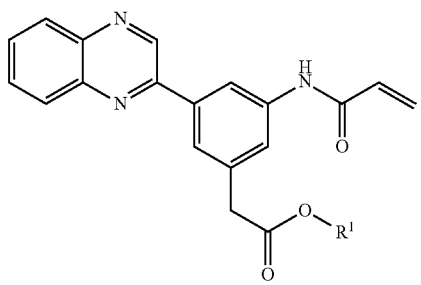

wherein $R^1$ is H or $C_1$-$C_6$ alkyl; or pharmaceutically acceptable salt thereof.

In some embodiments, the JAK3 inhibitor compound is a compound of formula 2:

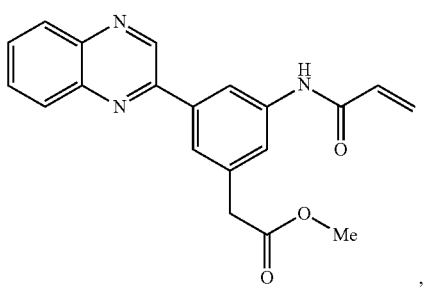 [SMILES: C=CC(=O)Nc1cc(CC(=O)OC)cc(-c2cnc3ccccc3n2)c1]

or pharmaceutically acceptable salt thereof.

In some embodiments, the JAK3 inhibitor compound is a compound of formula 3:

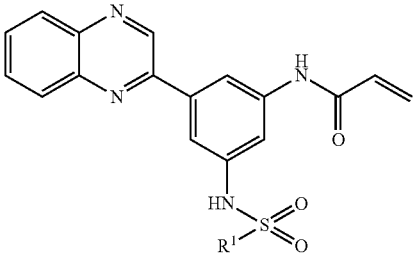

wherein $R^1$ is H or $C_1$-$C_6$ alkyl; or pharmaceutically acceptable salt thereof. In some embodiments, $R^1$ is methyl.

Some embodiments include a pharmaceutical composition comprising a therapeutically effective amount of one or more of the disclosed JAK3 inhibitor compounds or a pharmaceutically acceptable salt thereof, and one or more pharmaceutically acceptable excipients.

Some embodiments include a pharmaceutical composition consisting essentially of a therapeutically effective amount of one or more of the disclosed JAK3 inhibitor compounds or a pharmaceutically acceptable salt thereof, and one or more pharmaceutically acceptable excipients.

Some embodiments include a pharmaceutical composition consisting of a therapeutically effective amount of one or more of the disclosed JAK3 inhibitor compounds or a pharmaceutically acceptable salt thereof, and one or more pharmaceutically acceptable excipients.

The compounds of embodiments herein are JAK3 selective inhibitor compounds, as evidenced by the data in Table 1, below. The data presented in Table 1 below were obtained from two independent analyses which confirm that each of compounds 1a, 1b, 2, and 3 are highly selective for JAK3 compared to JAK1, JAK2, and TYK2. Compound 1b, in particular, is also highly and consistently soluble at pH 7.4.

TABLE 1

| | Compound Properties | | | | | | | | |
|---|---|---|---|---|---|---|---|---|---|
| Compound ID | JAK3 IC50 (uM) Original/ re-test | STAT5 IC50 (uM) Original/ re-test | JAK1 IC50 (uM) Original/ re-test | JAK2 IC50 (uM) Original/ re-test | TYK2 IC50 (uM) Original/ re-test | MW (free base) | cLog P | tPSA ($A^2$) | Solubility pH 7.4** (uM) Original/ Re-test |
| 1a | 0.013/0.010 | 1.2/2.9 (178X)* | 100/100 | 100/100 | 100/100 | 401.46 | 2.99 | 77.37 | 85/34 |
| 1b | 0.018/0.018 | 5.5/8.6 (392X)* | 100/100 | 100/100 | 100/100 | 387.43 | 2.27 | 86.16 | 88/88 |
| 2 | 0.013/0.007 | 0.8/2.9 (370X)* | 100/100 | 100/100 | 100/100 | 347.37 | 2.56 | 80.12 | 9/1 |

TABLE 1-continued

Compound Properties

| Compound ID | JAK3 IC50 (uM) Original/ re-test | STAT5 IC50 (uM) Original/ re-test | JAK1 IC50 (uM) Original/ re-test | JAK2 IC50 (uM) Original/ re-test | TYK2 IC50 (uM) Original/ re-test | MW (free base) | cLog P | tPSA (A²) | Solubility pH 7.4** (uM) Original/ Re-test |
|---|---|---|---|---|---|---|---|---|---|
| 3 | 0.016/0.023 | 7.5/7.4 (382X)* | 100/100 | 100/100 | 100/100 | 368.41 | 1.86 | 99.99 | 34/3 |

*JAK3 selectivity vs. STAT5
**Solubility in aqueous buffer
JAK3 selectivity vs. JAK1, JAK2, TYK2 >5000X for all compounds As seen in Table 1, each of the compounds is more than 5000 times more selective for JAK3 than for JAK1, JAK2, or TYK2. Thus, each is highly selective for JAK3.

Kinase Panel: These compounds were tested against 439 kinases. Each compound was tested at a concentration of 1 µM, in duplicate and in the presence of 10 µM ATP. Curve fits were performed where the enzyme activities <65%. The compounds were further profiled in an Exemplary Kinase Panel Analysis against 14 kinases, along with staurosporine controls. In these studies, an IC50 was evaluated for each compound by testing, in duplicate (N=2), 10 compound concentrations based on 3-fold serial dilutions starting at 5 µM. The results are presented in Table 2 below, where empty cells indicate no inhibition or compound activity that could not be fit to an $IC_{50}$ curve.

TABLE 2

Exemplary Kinase Panel Analysis

| Kinase | Compound $IC_{50}$ (M) | | | | |
|---|---|---|---|---|---|
| | 1a | 2 | 1b | 3 | Staurosporine |
| CK1g1 | 5.88E−07 | 8.02E−08 | 7.38E−07 | 1.09E−07 | 1.33E−05 |
| CK1g2 | 2.48E−07 | 9.86E−09 | 3.22E−07 | 3.33E−08 | 5.09E−07 |
| CK1g3 | 3.58E−07 | 2.44E−08 | 7.57E−07 | 1.18E−07 | 1.61E−06 |
| EGFR | 3.70E−07 | | 2.86E−06 | | 7.13E−08 |
| EGFR (d746-750) | 3.45E−07 | | 2.29E−06 | | 1.15E−08 |
| EGFR (d746-750/T790M) | 8.79E−08 | 2.99E−07 | 5.60E−07 | 9.96E−07 | 1.82E−10 |
| EGFR (d752-759) | 1.94E−07 | 1.03E−06 | 1.56E−06 | 3.18E−06 | 5.52E−08 |
| EGFR (G719C) | 6.61E−08 | 4.23E−07 | 1.93E−07 | | 1.60E−07 |
| EGFR (L858R, T790M) | 2.31E−07 | 6.53E−07 | 1.32E−06 | 1.12E−06 | 2.23E−10 |
| EGFR (L861Q) | 3.52E−07 | | 2.65E−06 | | 6.57E−08 |
| EGFR (T790M) | 6.88E−07 | 3.31E−06 | 3.54E−06 | 2.24E−06 | 1.59E−09 |
| ITK | 7.21E−08 | 3.49E−08 | 6.80E−08 | 2.78E−07 | 1.94E−09 |
| JAK3 | 1.57E−09 | 1.19E−09 | 9.72E−10 | 2.49E−08 | <7.63E−11 |
| TXK | 3.16E−08 | 1.49E−08 | 1.61E−08 | 1.44E−07 | 6.72E−09 |

Throughout testing, the compounds were found to be selective for JAK3. These compounds are promising, highly specific JAK3 inhibitors.

Some exemplary data of the JAK3 inhibitor compounds are shown in Table 3 below. In some instances, some analyses were carried out in two separate and distinct sessions. The resultant data is separated by a "/" where appropriate.

TABLE 3

Consolidated Data

| | Compound ID | | | |
|---|---|---|---|---|
| | 1a | 1b | 2 | 3 |
| JAK3 biochemical IC50 [uM] | 0.013/0.010 | 0.018/0.018 | 0.015/0.007 | 0.016/0.023 |
| STAT5 inhibition IC50 [uM] | 1.2/2.9 | 5.5/8.6 | 0.8/2.9 | 7.5/7.4 |
| MW | 401.46 | 387.43 | 347.37 | 368.41 |
| ClogP | 2.99 | 2.27 | 2.56 | 1.86 |
| tPSA [A²] | 77.37 | 86.16 | 80.12 | 99.99 |
| Solubility, pH 7.4 [uM] | 85/34 | 88/88 | 9/1 | 34/3 |

TABLE 3-continued

Consolidated Data

| | Compound ID | | | |
|---|---|---|---|---|
| | 1a | 1b | 2 | 3 |
| Brain penetration classification | Low | Low | Moderate | Low |
| Human Liver Microsomes t½ (min) | 64/60 | 75/>60 | (>1000)*/5.5 | 58/60 |
| Rat Liver Microsomes t½ (min) | 50/36 | 63/77 | 2/2.2 | 38/60 |
| Mouse Liver Microsomes t½ (min) | 7.3/15 | 23.0/50 | 3.3/6 | 25.0/84 |
| CYP1A2 IC$_{50}$ [uM] LCMS | 34/>100 | >100/>100 | 90/5.1 | >100/>100 |
| CYP2C19 IC$_{50}$ [uM] LCMS | >100/90 | >100/>100 | >100/95 | >100/59 |
| CYP2D6 IC$_{50}$ [uM] LCMS | >100/>100 | >100/>100 | >100/>100 | >100/>100 |
| CYP3A4 IC$_{50}$ [uM] midazolam LCMS | >100/>100 | >100/>100 | >100/>100 | >100/>100 |
| CYP3A4 K$_{50}$ [uM] testosterone LCMS | 81.5/>100 | >100/>100 | >100/>100 | 89.7/51 |
| CYP2B6 IC50 [uM] LCMS | NT | NT | NT | NT |
| CYP2C8 IC50 [uM] LCMS | NT | NT | NT | NT |
| CYP2C9 IC50 [uM] LCMS | NT | NT | NT | NT |
| Human Plasma protein binding (%) | 77.7 ± 3.3 | 68.3 ± 5.4 | 87.7 ± 1.1 | 94.6 ± 0.5 |
| Mouse Plasma protein binding (%) | 96.6 ± 1.2 | 94.1 ± 1.7 | ND* | 85.3 ± 0.4 |

The compounds display favorable safety profiles based on AMES, hERG, and cytotoxicity testing, as shown in Table 5.

TABLE 5

Safety profile

| | | hERG (K$^+$ channel current in HEK293 cells) IC50 (μM) | Cytotoxicity Screening L929 Fibroblasts | |
|---|---|---|---|---|
| Compound ID | AMES test | | Minimal Effective Concentration* (MEC, uM) | 50% Maximal Effect Concentration** (AC50, uM) |
| 1a | Not mutagenic | >10 | 9 | 20 |
| 1b | Not mutagenic | >10 | 20 | 45 |
| 2 | Not mutagenic | >10 | 2 | 18 |
| 3 | Not mutagenic | >1 | 10 | 20 |

The cytotoxicity screening panel included cell count, nuclear size, DNA structure, cell membrane permeability, mitochondrial mass, mitochondrial membrane potential, and cytochrome C release.

The JAK3 inhibitor compounds disclosed herein may be formulated as the free base or in a pharmaceutically acceptable salt form.

As used herein, "pharmaceutically acceptable salts" refers to derivatives of the disclosed JAK3 inhibitor compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the disclosed JAK3 inhibitor compounds include the conventional non-toxic salts of the parent compound formed, for example, from non-toxic inorganic or organic acids. The pharmaceutically acceptable salts of the disclosed JAK3 inhibitor compounds may be synthesized from the parent compound which contains a basic or acidic moiety by conventional chemical methods. In some embodiments, such salts can be prepared by reacting the free acid or base forms of these compounds with a stoichiometric amount of the appropriate base or acid in water or in an organic solvent, or in a mixture of the two. Generally, non-aqueous media like ether, ethyl acetate, ethanol, isopropanol, or acetonitrile (ACN) are preferred. Lists of suitable salts are found in *Remington's Pharmaceutical Sciences*, 17th ed., Mack Publishing Company, Easton, Pa., 1985, p. 1418 and *Journal of Pharmaceutical Science*, 66, 2 (1977), each of which is incorporated herein by reference in its entirety.

Some embodiments also includes quaternary ammonium salts of the compounds described herein, where the compounds are primary amines, secondary amines, or tertiary amines. As used herein, "quaternary ammonium salts" refers to derivatives of the disclosed primary amine, secondary amine, or tertiary amine compounds wherein the parent amine compounds are modified by converting the amines to quaternary ammonium cations via alkylation (and the cations are balanced by anions such as Cl$^-$, CH$_3$COO$^-$, or CF$_3$COO$^-$), for example methylation or ethylation.

In some embodiments, the pharmaceutically acceptable salts are selected from hydrochloride, oxalate, maleate, sulphate, nitrate, HBr, p-toluenesulphonate, or camphorsulfonate. The solubility of certain of these salts has been confirmed and presented in Table 4.

TABLE 4

Exemplary Salts

| Compound ID | Salt | Solubility In Aqueous Buffer | |
|---|---|---|---|
| | | pH 5.0 (µM) | pH 6.5 (µM) |
| 1b | Free base | 93 | 108 |
| 1b(A) | 2HCl | 1039 | 919 |
| 1b(B) | Oxalate | 1219 | 738 |
| 1b(C) | Maleate | 248 | 155 |
| 1b(H) | 2Sulphate | >1662 | 238 |
| 1b(L) | N'trate | 557 | 207 |
| 1b(M) | 2HBr | 1157 | 602 |
| 1b(N) | 1,5 p-toluenesulphonate | 815 | 441 |
| 1b(⊢) | Camphorsulfonate | 339 | 96.2 |

In some embodiments, these compounds, pharmaceutically acceptable salts, and compositions are useful in methods for inhibiting JAK3 activity and for the treatment of JAK3-associated diseases, disorders, or conditions, particularly those involving the immune system, autoimmune diseases, an allergic or type I hypersensitivity reactions, hair-loss disorders, and skin disorders.

As used herein, the term "alkyl" is meant to refer to a saturated hydrocarbon group which is straight-chained or branched. Example alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 20, from 2 to about 20, from 1 to about 10, from 1 to about 8, from 1 to about 6, from 1 to about 4, or from 1 to about 3 carbon atoms.

In some embodiments, some compounds described herein can be asymmetric (e.g., having one or more stereocenters). All stereoisomers, such as enantiomers and diastereomers, are intended unless otherwise indicated. In some embodiments, compounds of embodiments herein that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C═N double bonds, and the like can also be present in the compounds described herein, and all such stable isomers are contemplated in the present invention. Cis and trans geometric isomers of the compounds described may be isolated as a mixture of isomers or as separated isomeric forms. Where a compound capable of stereoisomerism or geometric isomerism is designated in its structure or name without reference to specific R/S or cis/trans configurations, it is intended that all such isomers are contemplated.

Resolution of racemic mixtures of compounds can be carried out by any of numerous methods known in the art. An example method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as α-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

In some embodiments, resolution of racemic mixtures can also be carried out by elution on a column packed with an optically active resolving agent (e.g., dinitrobenzoylphenylglycine). Suitable elution solvent composition can be determined by one skilled in the art.

Some JAK3 inhibitor compounds may also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, amide-imidic acid pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

In some embodiments, the disclosed JAK3 inhibitor compounds further include deuterates, racemates, enantiomers, hydrates, solvates, as well as anhydrous and non-solvated forms.

The term, "compound," as used herein is meant to include all stereoisomers, geometric isomers, tautomers, and isotopes of the structures depicted.

In some embodiments, the disclosed JAK3 inhibitor compounds and pharmaceutically acceptable salts thereof, can be prepared or present together with other substances such as water and solvents (e.g. hydrates and solvates) or can be isolated.

The disclosed JAK3 inhibitor compounds can also include all isotopes of atoms occurring in the intermediates or final compounds. Isotopes include those atoms having the same atomic number but different mass numbers. For example, isotopes of hydrogen include tritium and deuterium.

In some embodiments, the JAK3 inhibitor compounds, or salts thereof, are substantially isolated. By "substantially isolated" is meant that the compound is at least partially or substantially separated from the environment in which is formed or detected. Partial separation can include, for example, a composition enriched in the JAK3 inhibitor compound. Substantial separation can include compositions containing at least about 50%, at least about 60%, at least about 70%, at least about 80%, at least about 90%, at least about 95%, at least about 97%, or at least about 99% by weight of the JAK3 inhibitor compound, or salt thereof. Methods for isolating compounds and their salts are routine in the art.

In some embodiments, JAK3 inhibitor compounds are intended to include compounds with stable structures. As used herein, "stable compound" and "stable structure" are meant to indicate a compound that is sufficiently robust to survive isolation to a useful degree of purity from a reaction mixture, and formulation into an efficacious therapeutic agent.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Synthesis

In some embodiments, JAK3 inhibitor compounds, including salts thereof, can be prepared using known organic synthesis techniques and can be synthesized according to any of numerous possible synthetic routes.

The reactions for preparing JAK3 inhibitor compounds can be carried out in suitable solvents which can be readily selected by one of skill in the art of organic synthesis. In some embodiments, suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of JAK3 inhibitor compounds can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis*, 3$^{rd}$ Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC) or thin layer chromatography (TLC).

The JAK3 inhibitor compounds described herein can be prepared according to the original synthetic procedures described below.

Scheme 1

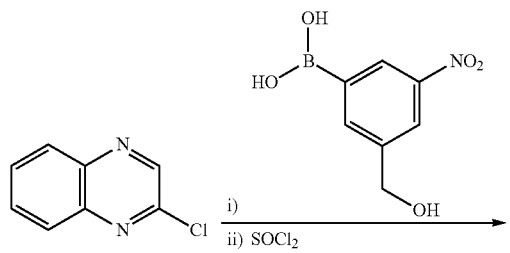

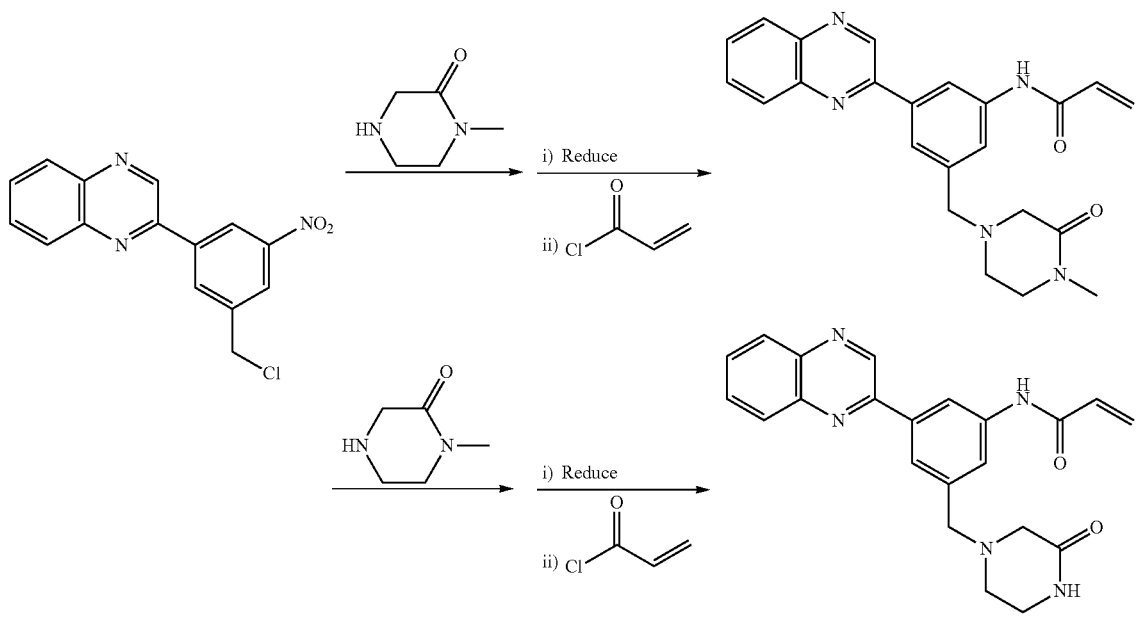

-continued
Scheme 2
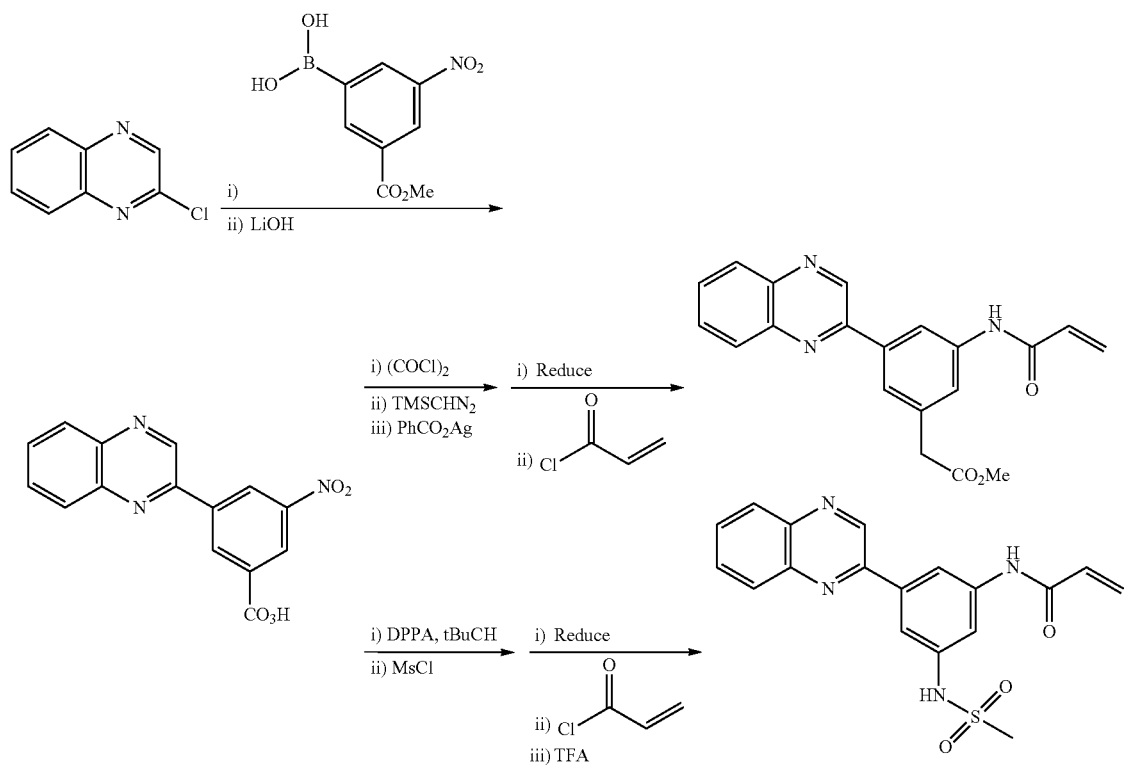
These methods resulted in low yields and improved synthesis methods were explored.
Scheme 3 Synthesis of compound 1A:
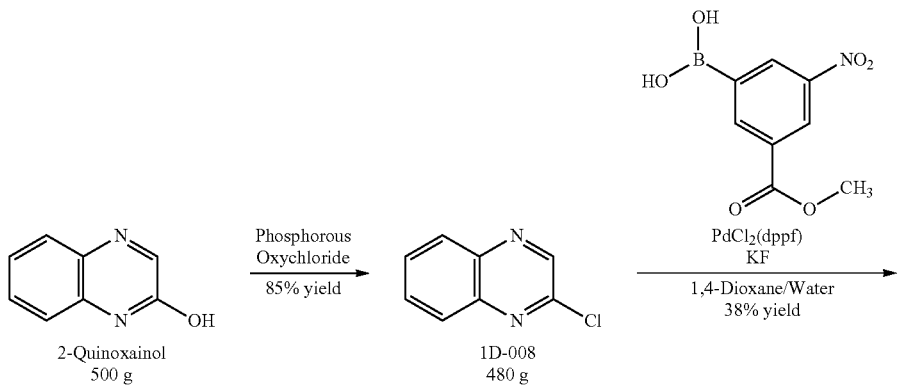

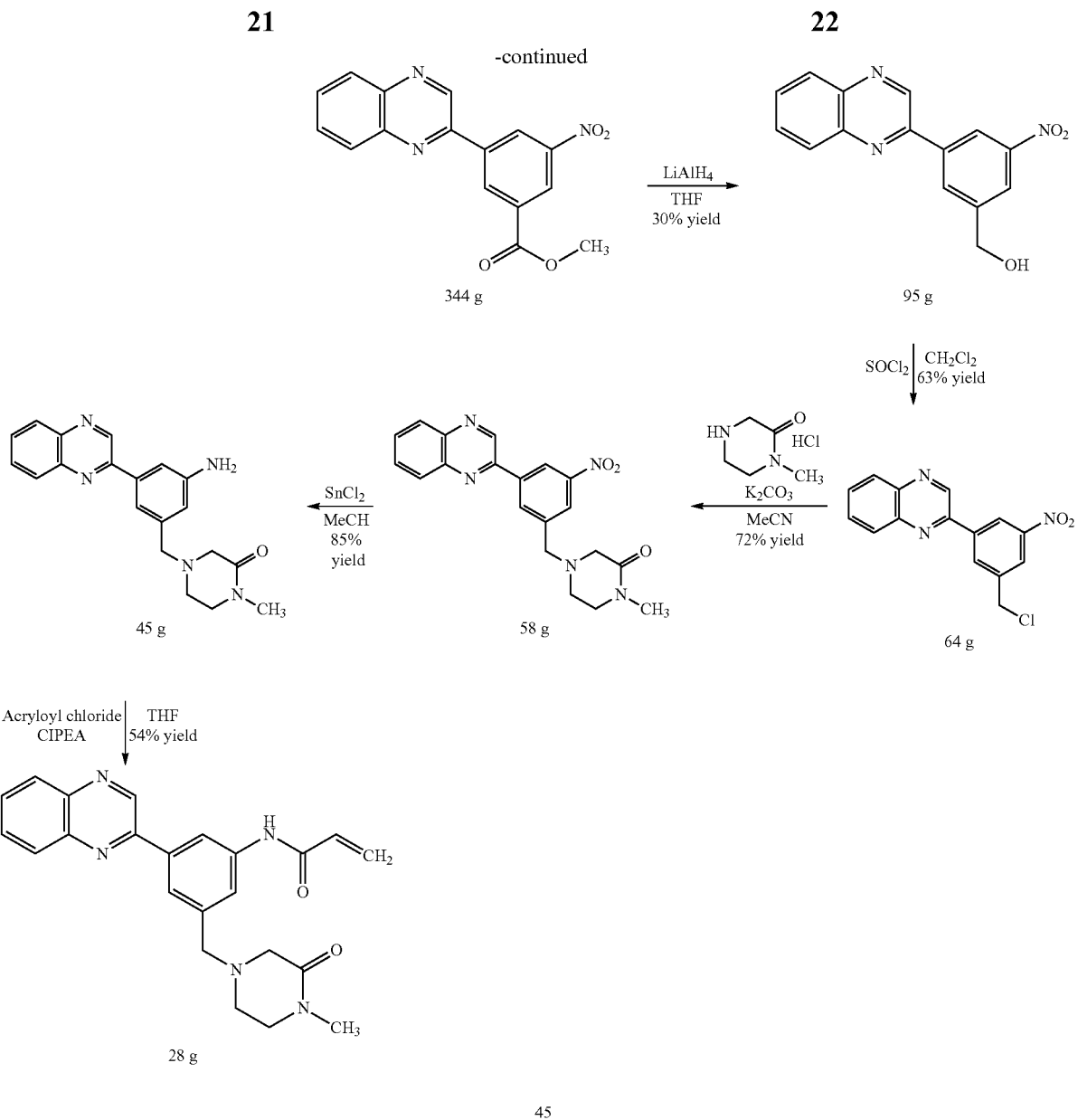
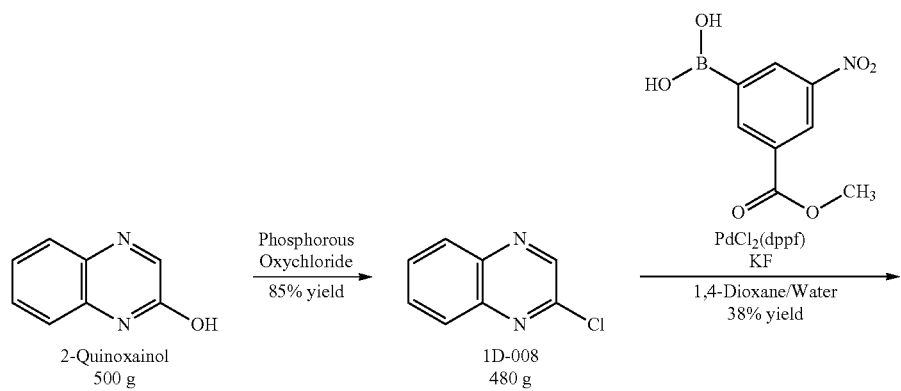
Scheme 4 synthesis of compound 1b

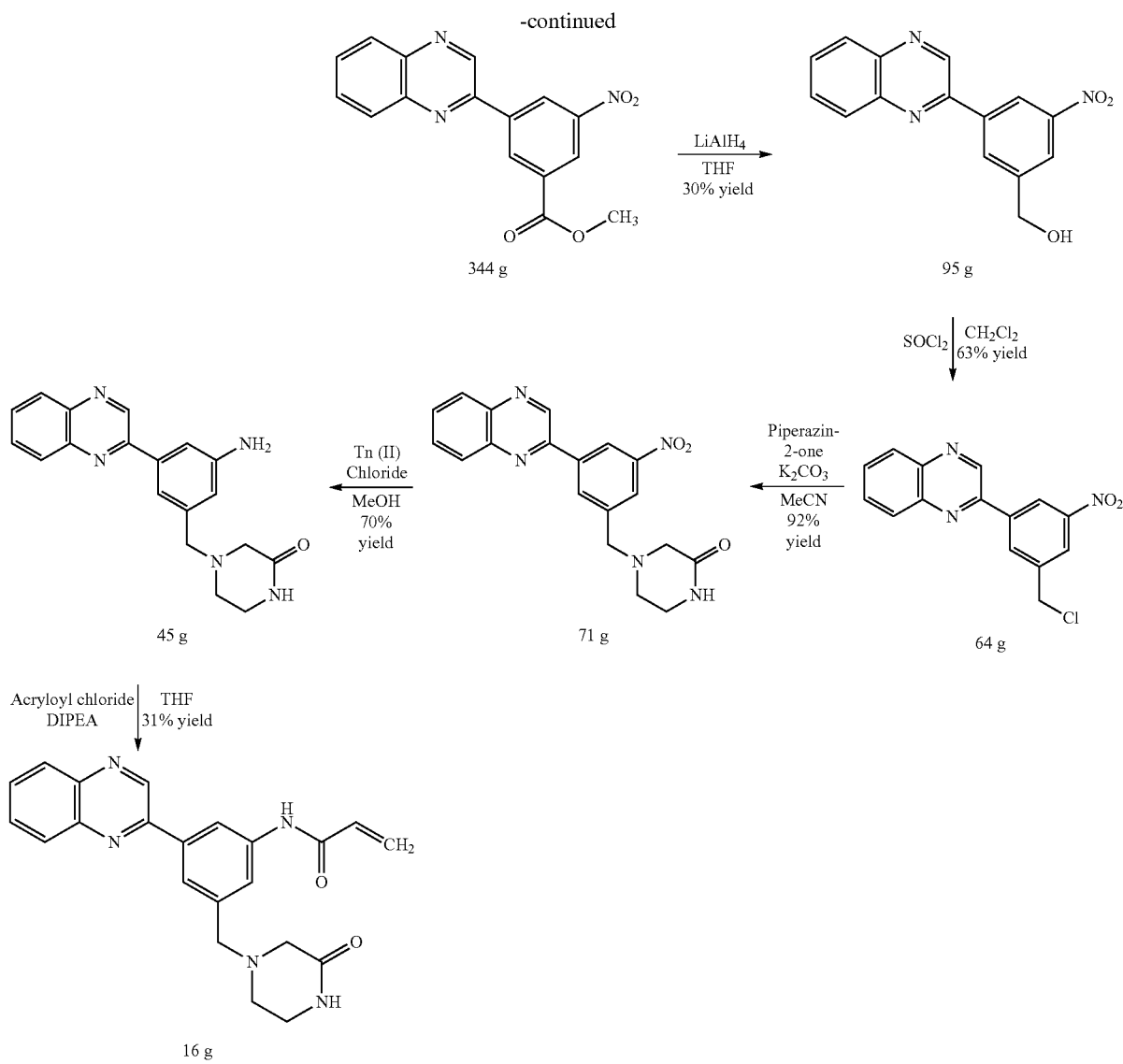
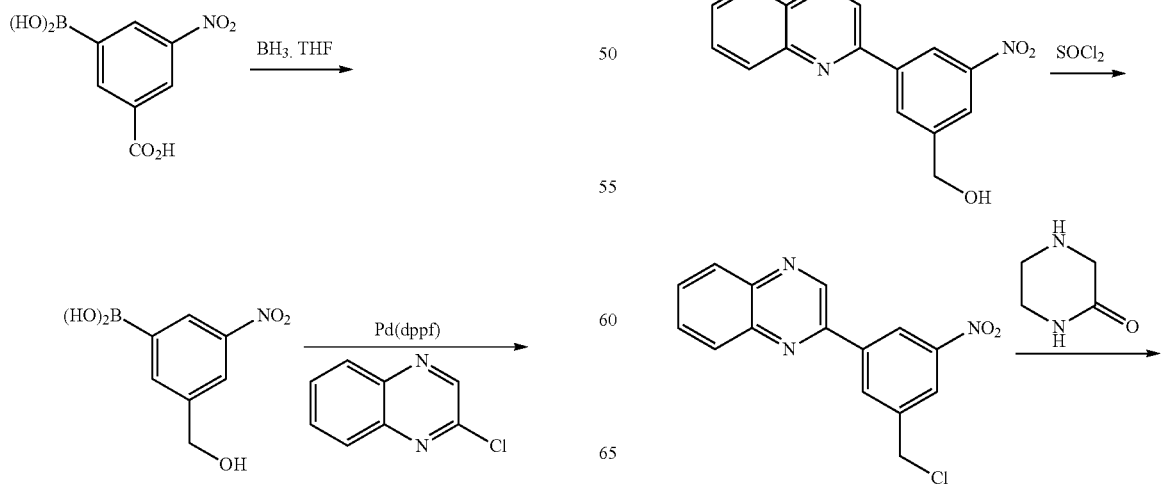
Scheme 5: Synthesis of an acid salt of compound 1b:

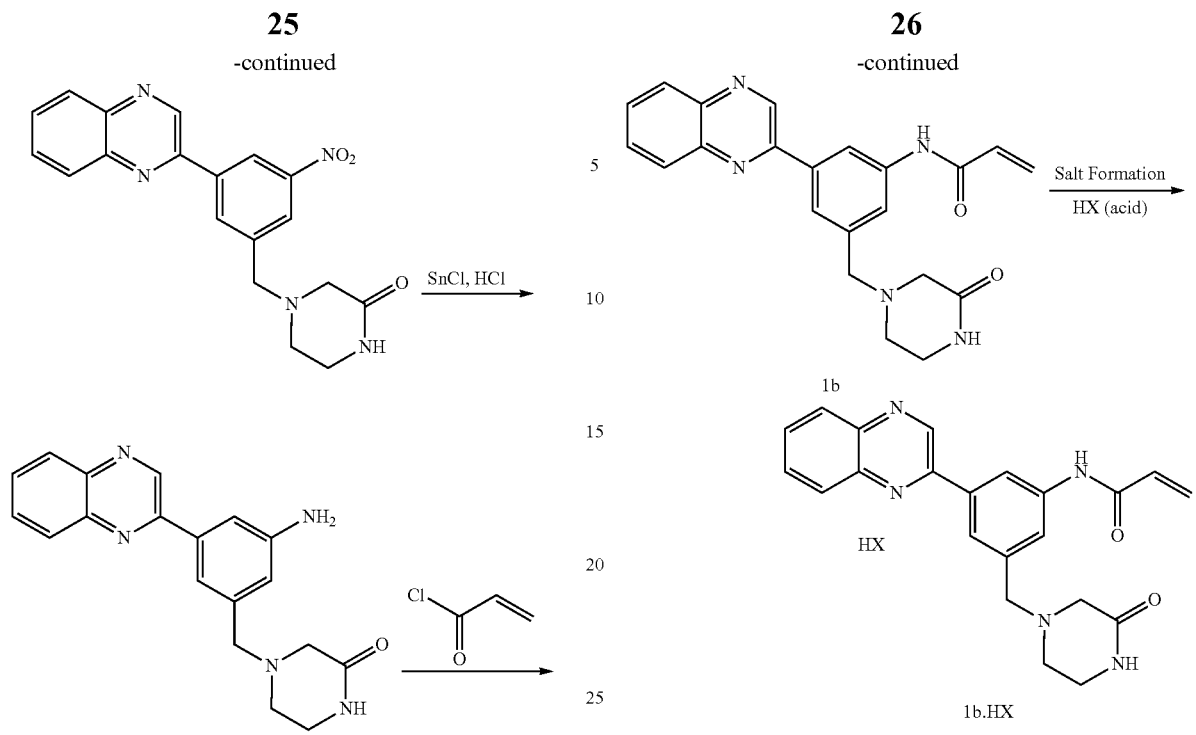
The above is a seven-step linear synthesis. Salt formation yields in the range of 36-77% depending on salt. Potential exists for a more convergent route that will allow greater control over starting materials.
Scheme 6: Synthesis of an acid salt of compound 2:
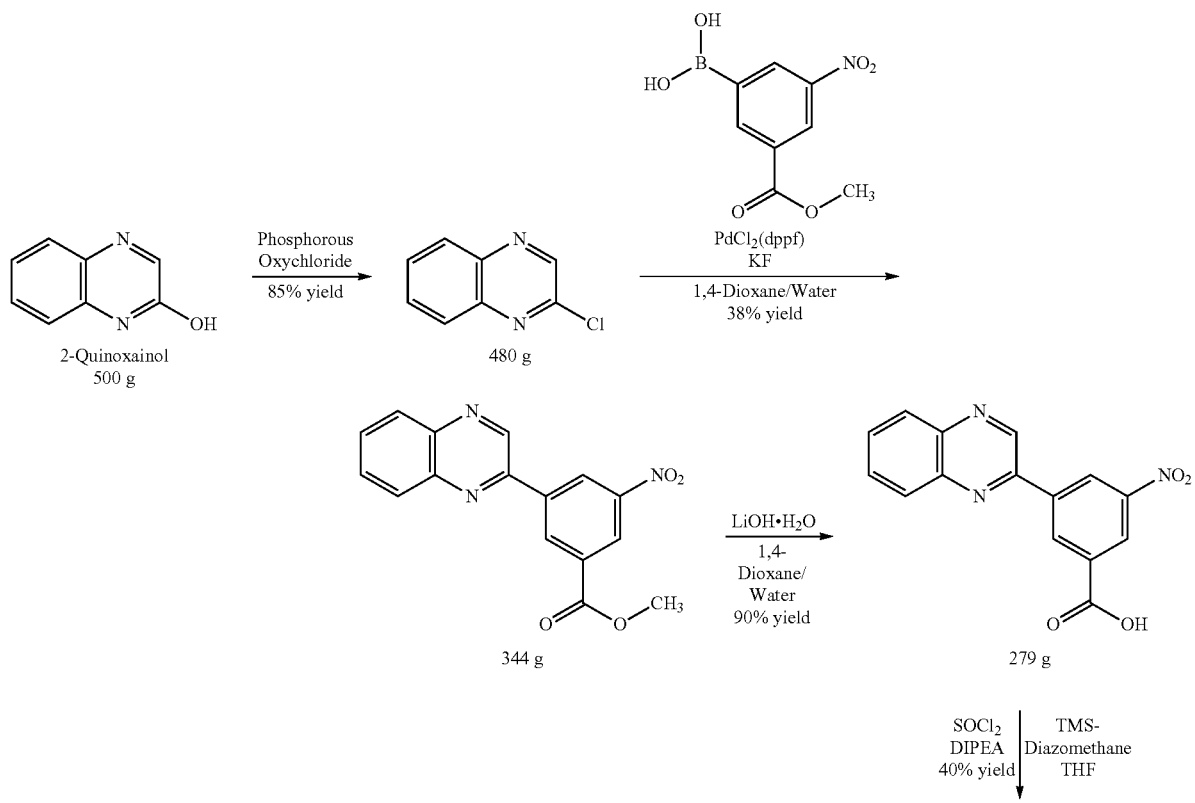

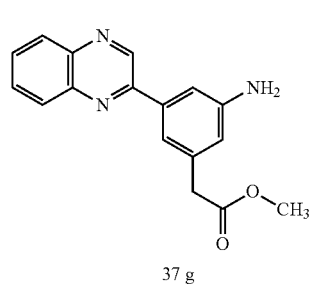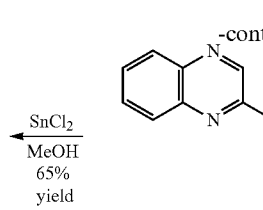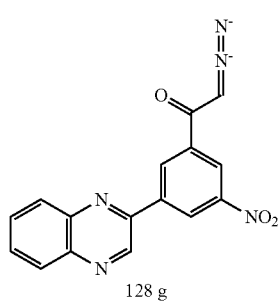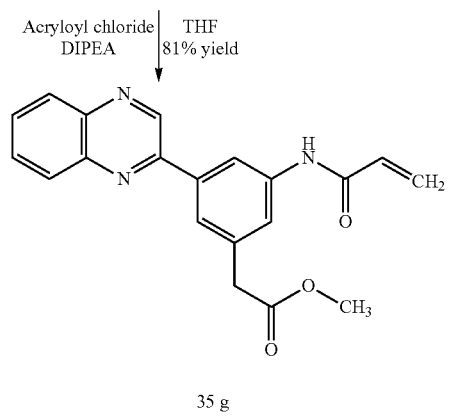
Scheme 7: synthesis of compound 3
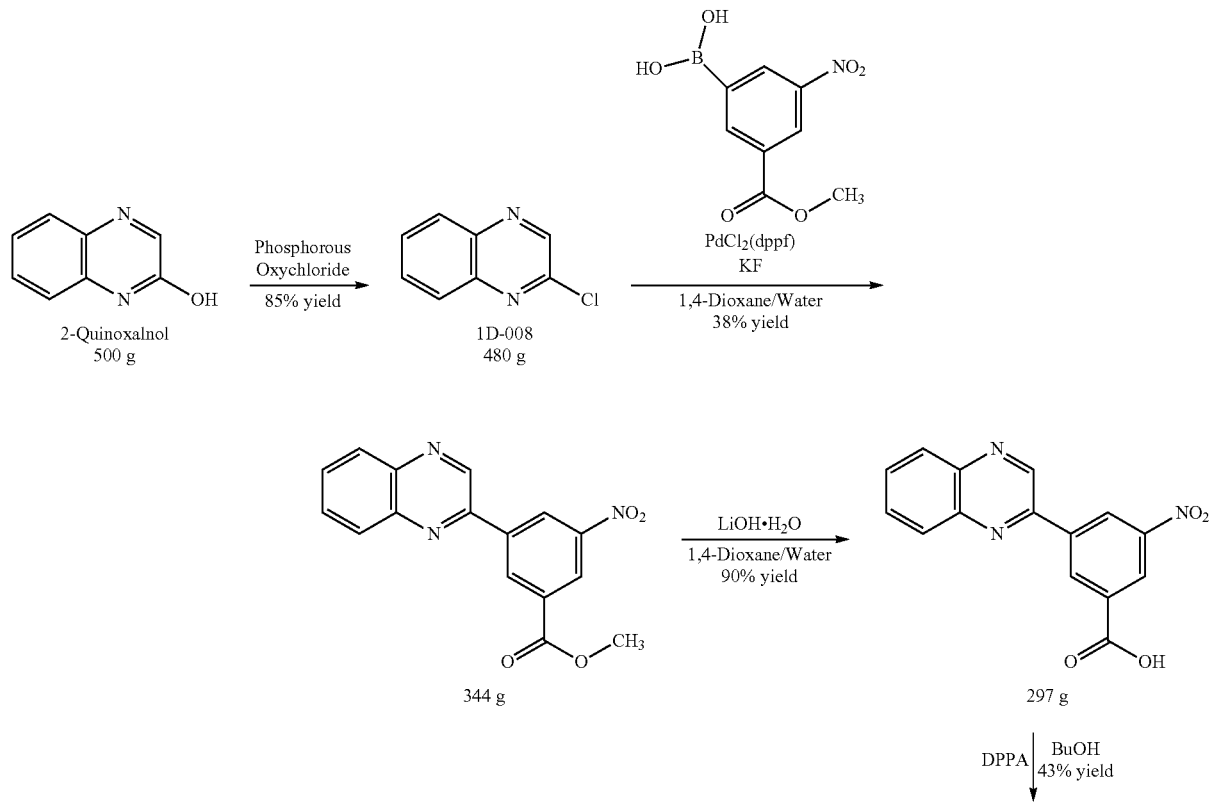

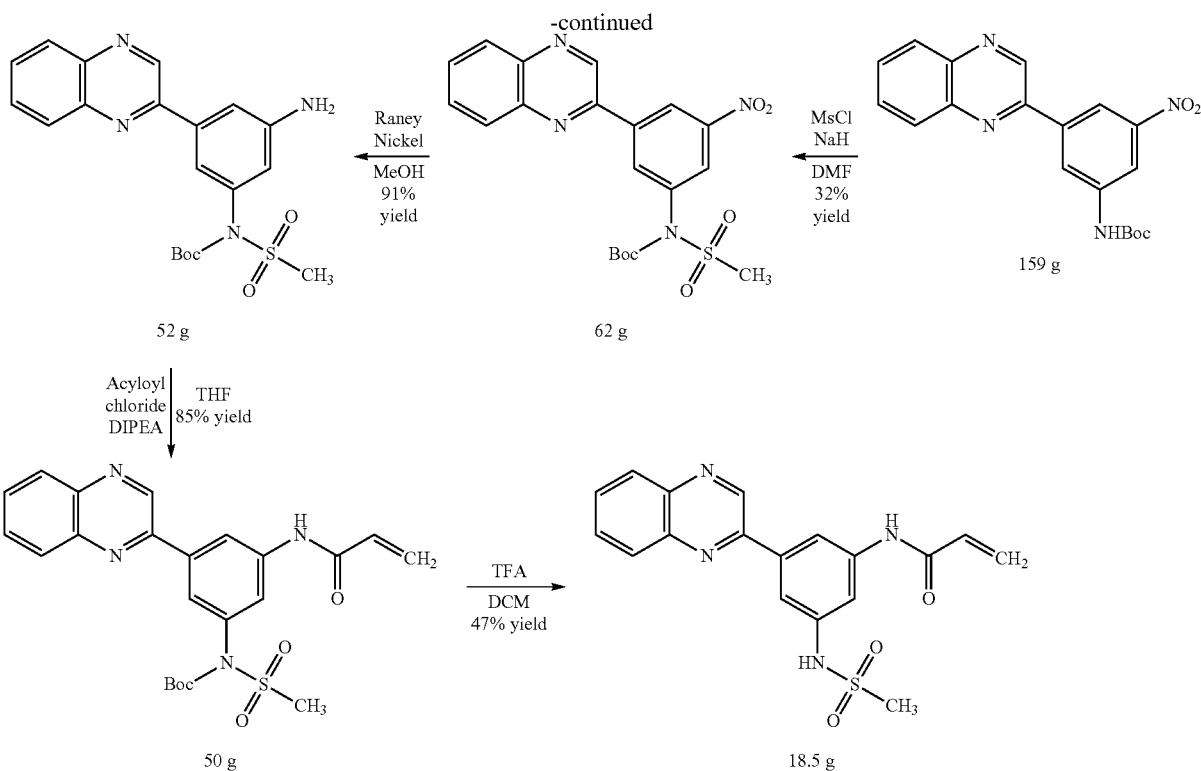

The above synthetic routes represent initial steps taken to synthesize the compounds described herein. Further efforts were conducted to provide more robust syntheses, as discussed below in relation to compound 1b.

Synthesis of N-[3-[(3-oxopiperazin-1-yl) methyl]-5-quinoxalin-2-yl-phenyl] prop-2-enamide (Compound 1b)

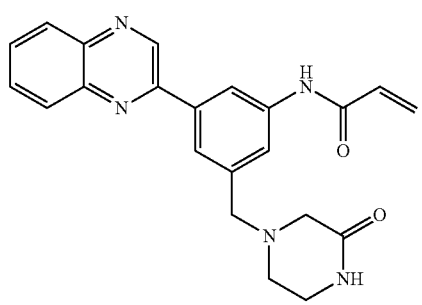 [SMILES: C=CC(=O)Nc1cc(CN2CCNC(=O)C2)cc(-c2cnc3ccccc3n2)c1]

One early approach to synthesizing Compound 1b, and its pharmaceutically acceptable salts involved the medicinal chemistry approach below:

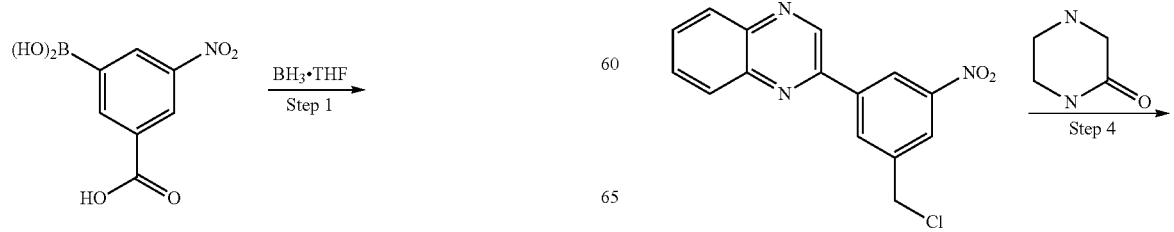

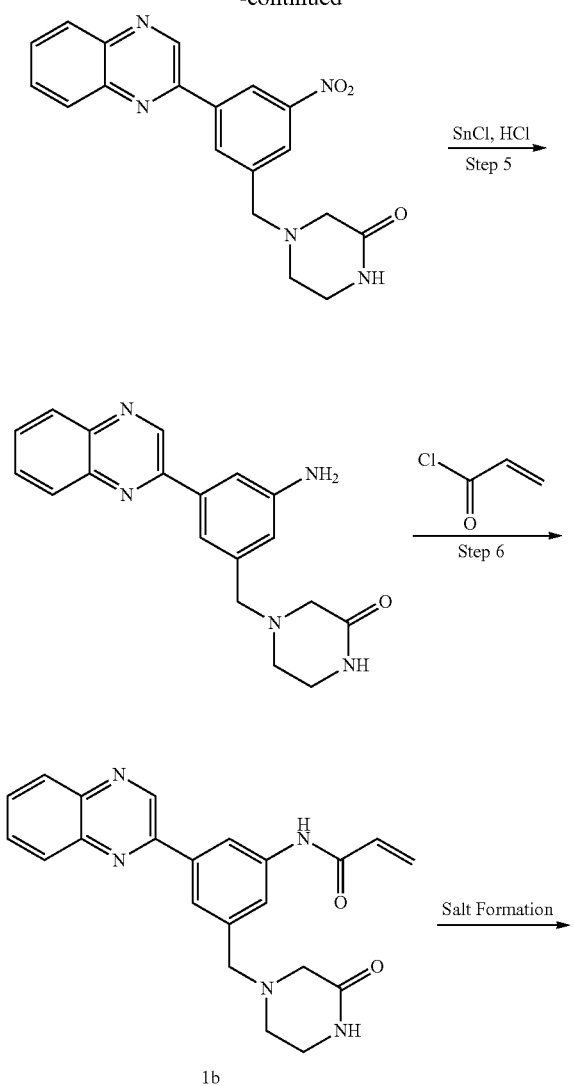

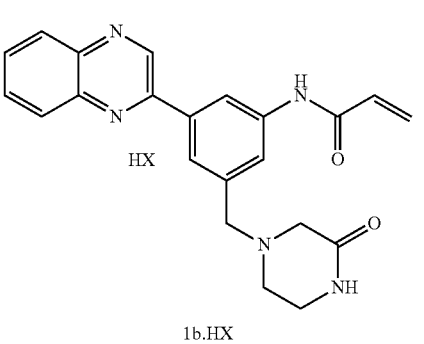

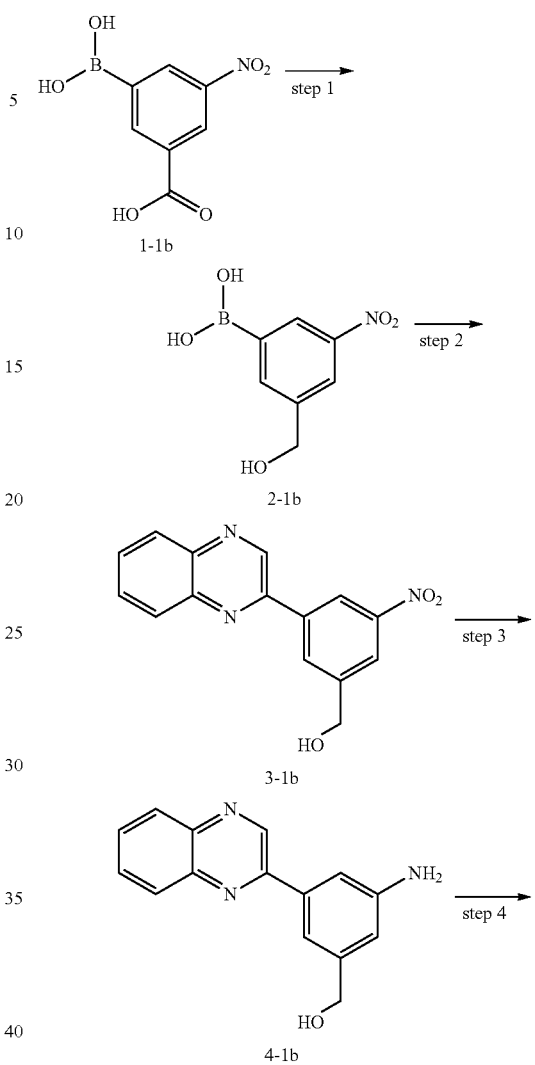

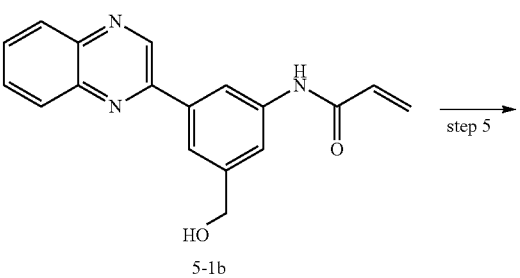

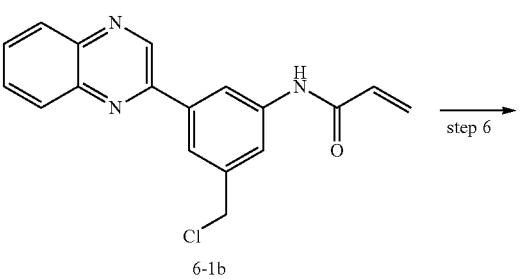

This method suffers from large variability in yield and employs materials that may not be practical for large scale production. Accordingly, several new routes for the synthesis of Compound 1b have been proposed the with new route resulting from modification of the Medicinal Chemistry route described above provided good results.

This new route uses commercially available 3-Carboxy-5-nitrophenylboronic acid as a starting material.

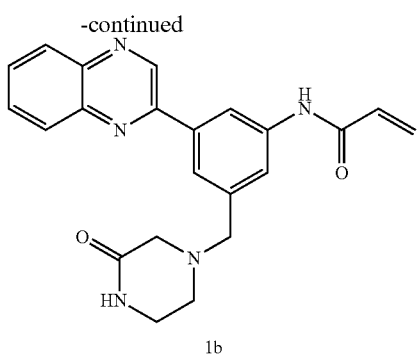

1b

The reduction of the carboxylic acid moiety to the benzyl alcohol 2-1b and Suzuki coupling during the second step were already validated when the Medicinal chemistry route was investigated. Those two steps were very successful and high yielding to produce the nitro intermediate 3-1b. A new method to reduce the nitro group was identified using iron in presence of ammonium chloride that was high yielding and far more amenable for further scale-up compared to the previous tin chloride method. The acylation with acryloyl chloride of the amino 4-1b was carried out earlier in this synthetic route. A new method using a saturated solution of sodium bicarbonate in a biphasic mixture of THF and water has enabled selective acylation of the amine 4-1b giving the acryloyl amide 5-1b in good yield. Chlorination of the benzyl alcohol has been optimized by adding an excess of thionyl chloride in a hot solution of the alcohol in chloroform. Finally, the displacement of the chloride with piperazine-2-one was achieved with excess potassium carbonate at reflux in acetonitrile to afford 1b in relatively good yield. FIG. 1 depicts the process steps described herein.

Step 0: Preparation of Precursor Quinaxoline

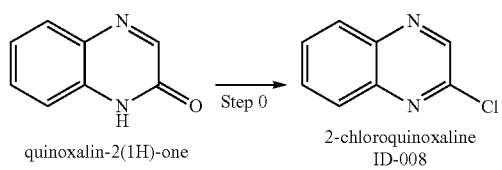

quinoxalin-2(1H)-one    2-chloroquinoxaline ID-008

The chlorination of the 2-hydroxy-quinoxaline was carried out in neat POCl3 (2.3 eqs) at reflux for an hour and produced the 2-chloro-quinoxaline (1D-008) in very good yield. This chemistry was tested on 100 g scale and afforded typically 103-105 g (98-99%). A quick filtration through a Pad of silica of the crude reaction mixture resulted in clean material (99% pure by LCMS). This reaction has been scaled up to 600 g.

Step 1: Preparation of 2-1b

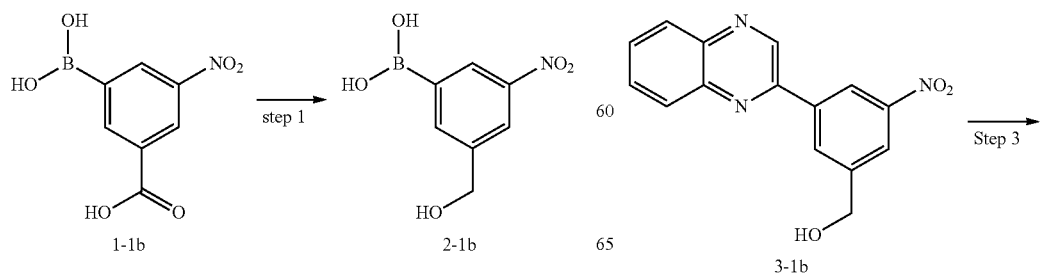

1-1b        2-1b

The reduction of the carboxylic acid group of the 3-Carboxy-5-nitrophenylboronic acid was tested numerous times on different scale (1-100 g) and has provided an optimized method. Typically the reduction of the carboxylic acid was carried out by adding 4 equivalents of borane tetrahydrofuran complex (1M in THF) added at 10° C. to a solution of the carboxylic acid in THF. The low temperature during the addition of the borane solution and the relatively high dilution of the acid were found critical to avoid any polymerization side reaction. Under those conditions, the benzyl alcohol is obtained very clean (90-99% pure by LCMS) with no major purification required. A quick extraction and a trituration of the crude solid in a mixture of ether and hexane provided the pure material.

Starting material boronic acid should be good quality, preferably having a purity of at least of 95%.

Step 2: Preparation of 3-1b

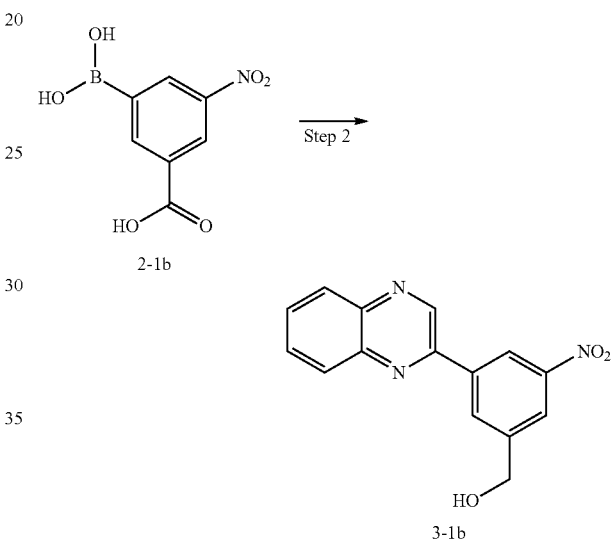

3-1b

The Suzuki coupling between the boronic acid (2-1b) and the 2-chloro-quinoxaline has been tested on several scales (10-100 g). Optimal conditions for coupling utilized equimolar quantities of boronic acid and chloride in the presence of 4 equivalents of sodium carbonate and 0.005 equivalent of PdCl$_2$(dppf) dichloromethane complex. This reaction is relatively quick (2-4 hours) when heated under reflux in a mixture of 1,4-dioxane/water. The product can be obtained very clean (purity ≥95%) after a simple precipitation of the product in water and trituration of the material in IMS and Ether. The yields obtained under these conditions were typically ≥70%.

Step 3: Preparation of 4-1b

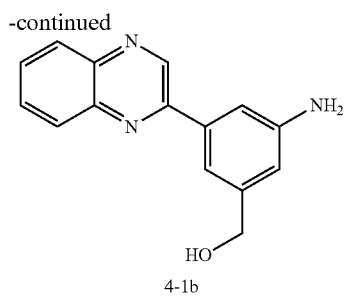

4-1b

Several conditions for the reduction of the nitro group of 3-1b were screened. In particular the hydrogenation of the nitro group has been extensively tested using different catalysts such as Pd/C and Raney nickel in a variety of solvents and also under several level of pressure of hydrogen. It was found that the lack of solubility of the starting material was a major issue to achieve complete reduction of the nitro group. It was found that when using acetic acid as a solvent or as a co-solvent but also when using high pressure of $H_2$ for a long period of time, some side products were detected that resulted from the reduction of the quinoxaline ring. The chemical reduction of the nitro group has also been tested using several reducing agents such as iron and sodium bisulfate. The best results were obtained when we used an excess (5 eqs) of iron in the presence of ammonium chloride (7 eqs) and a refluxed mixture of IMS and water. The reaction was quick and clean and produced a high yield of the expected amine 4-1b (typically ≥90%). The product can be isolated by precipitation in water and trituration of the material in IMS and $Et_2O$.

Note: Two successive filtrations of the hot reaction mixture through a pad of celite were required to remove all traces of iron from the material.

Step 4: Preparation of 5-1b

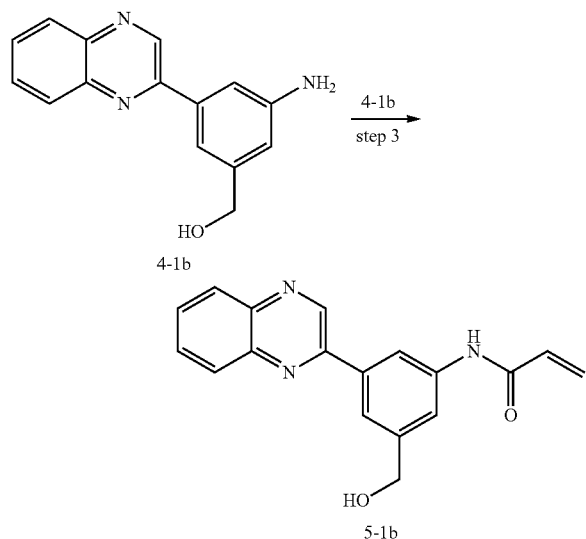

Several methods to obtain a regioselective acylation of the nitrogen versus the alcohol were screened to produce the acryloyl amide 5-1b (N-acylation of 4-1b). A strong base such as sodium hydride was tested in DMF or THF and produced mostly the N-acylated material but it was contaminated with a non-identified impurity (8.6%). Other organic bases such as trimethylamine or Hunig's base were also tested but we found that they produced a mixture of product and diacylated material (20%). The best results were obtained using a saturated solution of sodium bicarbonate in a biphasic mixture of THF and water. The reaction carried out at room temperature was relatively quick (4 hours) and provides mostly the N-acylated product (5-1b), typically with a purity≥95%. Only a limited amount (<4%) of the O-acylated side product was formed under these conditions. This reaction was tested on several scales (10-100 g) and produced a high yield ≥80%) of the expected acylated product 5-1b. The purification of the crude material was achieved by precipitation of the material in water and trituration of the crude solid in IMS and $Et_2O$.

Step 5: Preparation of 6-1b

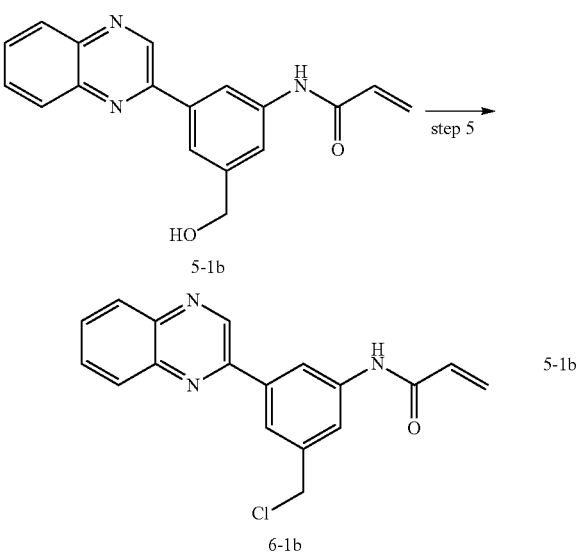

Several chlorination methods were tested on the alcohol 5-1b to generate the chloride 6-1b. Standard conditions such as excess thionyl chloride (2-3 eqs) in different chlorinated solvents (chloroform, dichloromethane) were attempted but the reactions did not go to completion. We noticed that longer reaction times (i.e. 12 hours of stirring at room temperature) produced a chlorinated side product. The low solubility of the benzyl alcohol 5-1b in the chlorinated solvents at room temperature was an issue. We have therefore tested the chlorination using thionyl chloride in other solvents (THF, DMF) but in all cases we found that reactions were messy, sluggish and/or incomplete. The best results were obtained when we added 3.5 equivalents of thionyl chloride into a hot solution of the benzyl alcohol (5-1b) in chloroform. The reaction under those conditions was relatively quick (less than 4 hours) and the formation of the non-soluble HCl salts of the product probably limits the formation of side products. The reaction is high yielding (typically >90%) and gives high purity (>95%) of the desired chloride 6-1b. The purification of the crude material is straightforward and can be achieve by precipitation of the crude material in water and subsequent trituration of the solid material in IMS and $Et_2O$.

Step 6: Preparation of compound 1b

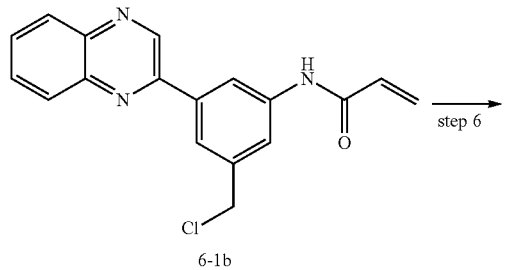

6-1b

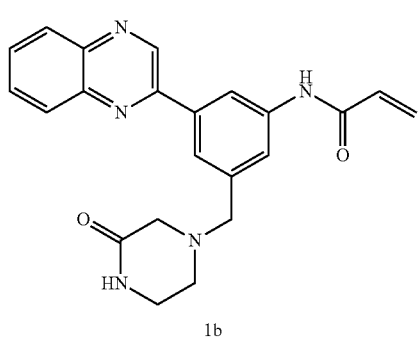 [SMILES: C=CC(=O)Nc1cc(CN2CCNC(=O)C2)cc(-c2cnc3ccccc3n2)c1]

1b

The original conditions to displace the chlorine of the intermediate 6-1b with piperazin-2-one used in the medicinal chemistry route have been validated on different scale (10-100 g) at this stage. This displacement was achieved in presence of an excess of potassium carbonate and placed under reflux of acetonitrile to afford 1b in a relatively good yield.

Methods

Some embodiments provide for a method of inhibiting an activity of JAK3 comprising contacting said JAK3 with a JAK3 inhibitor compound selected from:

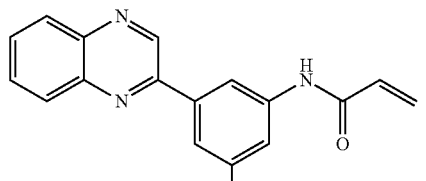

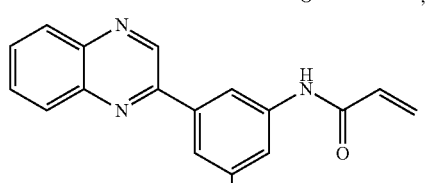

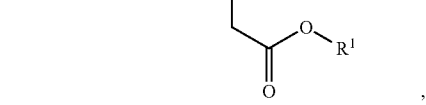

-continued

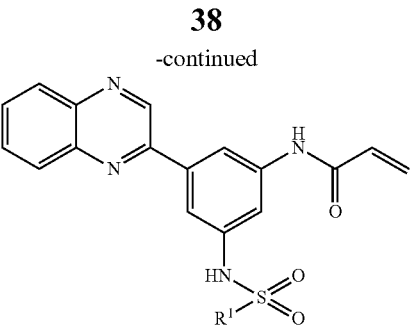

wherein $R^1$ is H or $C_1$-$C_6$ alkyl; or pharmaceutically acceptable salt thereof. In some instances, each $R^1$ is H or methyl.

Some embodiments provide for a method of inhibiting an activity of JAK3 consisting essentially of contacting said JAK3 with a JAK3 inhibitor compound selected from:

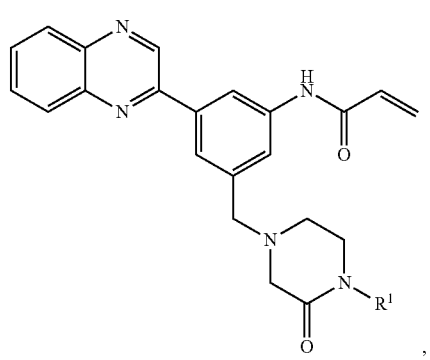

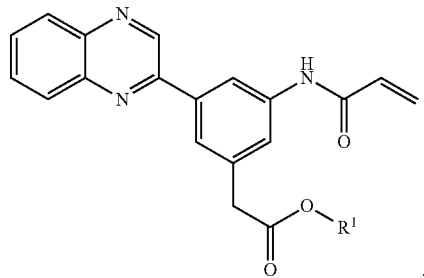

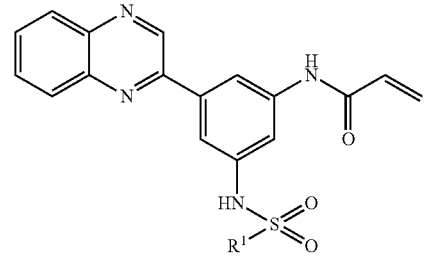

wherein $R^1$ is H or $C_1$-$C_6$ alkyl; or pharmaceutically acceptable salt thereof. In some instances, each $R^1$ is H or methyl.

Some embodiments provide for a method of inhibiting an activity of JAK3 consisting of contacting said JAK3 with a JAK3 inhibitor compound selected from:

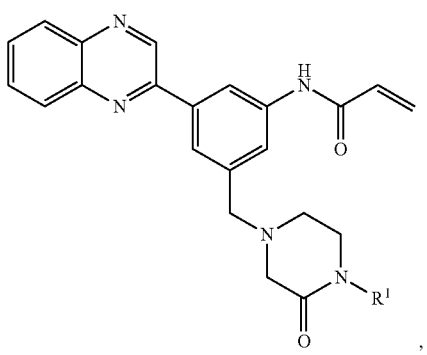

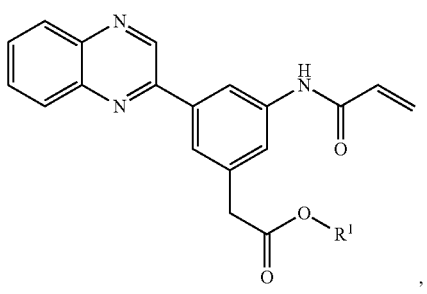

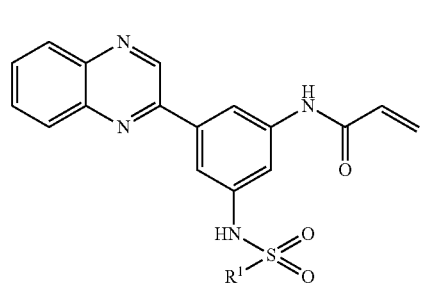

wherein $R^1$ is H or $C_1$-$C_6$ alkyl; or pharmaceutically acceptable salt thereof. In some instances, each $R^1$ is H or methyl.

Some embodiments provide a method of treating a JAK3-associated condition, disease, or disorder in a patient comprising administering to said patient a therapeutically effective amount of a JAK3 inhibitor compound selected from:

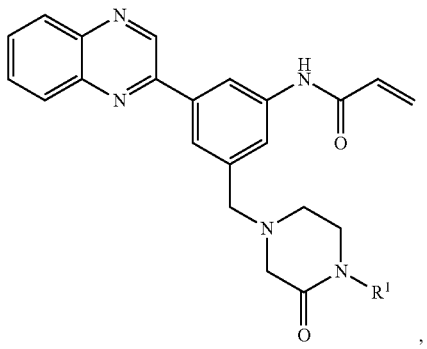

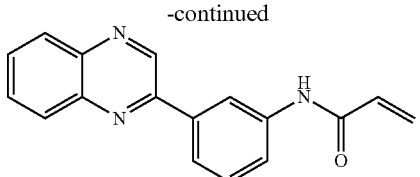

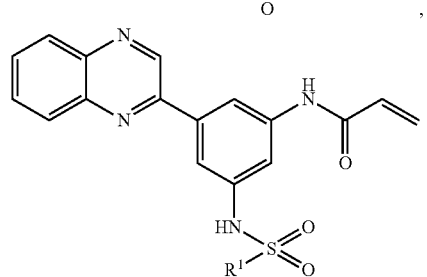

wherein $R^1$ is H or $C_1$-$C_6$ alkyl; or pharmaceutically acceptable salt thereof.

Some embodiments provide a method of treating a JAK3-associated condition, disease, or disorder in a patient consisting essentially of administering to said patient a therapeutically effective amount of a JAK3 inhibitor compound selected from:

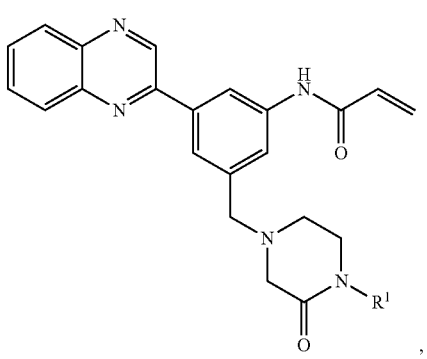

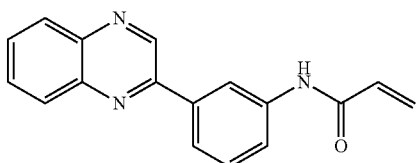

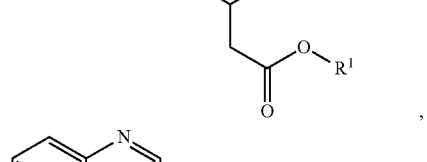

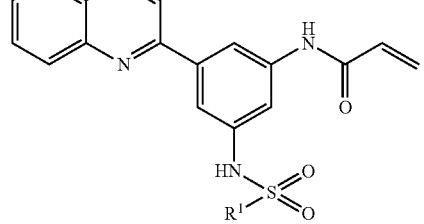

wherein R¹ is H or $C_1$-$C_6$ alkyl; or pharmaceutically acceptable salt thereof.

Some embodiments provide a method of treating a JAK3-associated condition, disease, or disorder in a patient consisting of administering to said patient a therapeutically effective amount of a JAK3 inhibitor compound selected from:

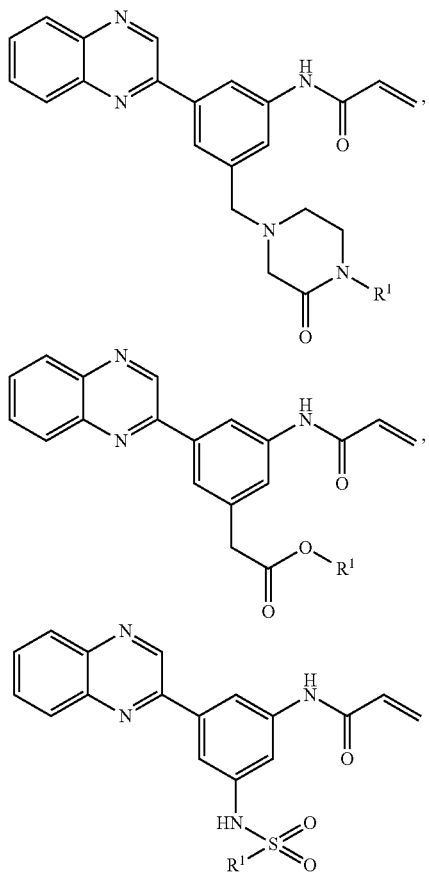

wherein R¹ is H or $C_1$-$C_6$ alkyl; or pharmaceutically acceptable salt thereof.

In some embodiments, the JAK3-associated disease, disorder or conditions treated are selected from one involving the immune system, an autoimmune disease, an allergic or type I hypersensitivity reaction, hair-loss disorders, or a skin disorder.

In some embodiments, JAK3-associated diseases, disorders, or conditions involving the immune system may be selected from organ transplant rejection, allograft rejection, and graft versus host disease (GVHD), mast cell mediated immediate hypersensitivity reaction, platelet aggregation, or thrombus formation.

JAK3-associated autoimmune diseases, disorders, or conditions are selected from multiple sclerosis, rheumatoid arthritis, juvenile arthritis, psoriatic arthritis, type I diabetes, lupus, psoriasis, pruritis, inflammatory bowel disease, ulcerative colitis, Crohn's disease, vitiligo, ankylosing spondylitis, myasthenia gravis, immunoglobulin nephropathies, autoimmune thyroid disorders, an autoimmune bullous skin disorder, pemphigus vulgaris (PV), bullous pemphigoid (BP), or rheumatoid arthritis.

JAK3-associated allergic or type I hypersensitivity reaction diseases, disorders, or conditions are selected from urticaria, eczema, conjunctivitis, rhinorrhea, rhinitis, asthma, gastroenteritis, familial amyotrophic lateral sclerosis, lupus, including systemic lupus, erythematosus, chronic cutaneous lupus, discoid lupus, tumid lupus, lupus profundus, subacute cutaneous lupus erythematosus, neonatal lupus, drug-induced lupus, and local or generalized acute cutaneous lupus, multiple sclerosis, Type I diabetes and complications from diabetes, cancer, asthma, rhinitis, atopic dermatitis, autoimmune thyroid disorders, Alzheimer's disease, leukemia, and thrombus.

In some embodiments, JAK3-associated skin disorders, diseases, or conditions may be selected from vitiligo, psoriasis, psoriasis vulgaris, atopic dermatitis, alopecia areata, patchy alopecia areata, alopecia totalis, alopecia universalis, ophiasis pattern alopecia areata, sisaihpo pattern alopecia areata, androgenetic alopecia (male and female pattern hair loss), telogen effluvium, hypotrichosis, hereditary hypotrichosis simplex, scarring alopecia, lichen planopilaris, central centrifugal cicatricial alopecia, skin rash, skin irritation, skin sensitization, contact dermatitis, or allergic contact dermatitis. In some embodiments, the vitiligo may be selected from localized vitiligo, focal vitiligo, generalized vitiligo, segmental vitiligo, acral vitiligo, facial vitiligo, acrofacial vitiligo, mucosal vitiligo, confetti vitiligo, trichrome vitiligo, marginal inflammatory vitiligo, quadrichrome vitiligo, blue vitiligo, Koebner phenomenon, vulgaris vitiligo, mixed acrofacial, vulgaris vitiligo, or universal vitiligo. In some embodiments, the alopecia areata may be patchy alopecia areata, alopecia totalis, alopecia universalis, ophiasis pattern alopecia areata, or sisaihpo pattern alopecia areata.

It is further appreciated that certain features, which are, for clarity, described in the context of separate embodiments, can also be provided in combination in a single embodiment. Conversely, various features which are, for brevity, described in the context of a single embodiment, can also be provided separately or in any suitable subcombination.

Certain JAK3 inhibitor compounds have an $IC_{50}$ with respect to JAK3 less than about 1000 nM, 500 nM, 200 nM, 100 nM, 50 nM, 20 nM, 10 nM, 5 nM, 2 nM, or 1 nM. Accordingly, JAK3 inhibitor compounds can modulate activity of JAK3. The term "modulate" is meant to refer to an ability to increase or decrease the activity of JAK3. Accordingly, JAK3 inhibitor compounds can be used in methods of modulating a JAK3 by contacting the JAK3 with any one or more of the compounds or compositions described herein. In some embodiments, compounds of the present invention can act as inhibitors of JAK3. In further embodiments, the JAK3 inhibitor compounds can be used to modulate (e.g., inhibiting) activity of a JAK3 in an individual in need of modulation (e.g., inhibition) of the enzyme by administering a modulating (e.g., inhibiting) amount of a JAK3 inhibitor compound. In some embodiments, the modulating amount may be a therapeutically effective amount of the JAK3 inhibitor compound.

In some embodiments, the modulating (e.g. inhibiting) JAK3 is selective over other members of the JAK family [i.e., JAK1, JAK2, and TYK2]. In some embodiments, the compounds used in this disclosure show 25% or more of binding to JAK3 comparing to other members of the JAK family. In some embodiments, the IC50 of JAK3 inhibitor compounds with respect to JAK1, JAK2, or TYK2 is greater than 1 μM, 5 μM, 10 μM, 20 μM, 50 μM, 100 μM, or 200 μM. In some embodiments, the relative ratio of IC50 of the compounds with respect to JAK1, JAK2, or TYK2 to that with respect to JAK3 is greater than about 5:1, 10:1, 20:1, 50:1, 100:1, 200:1, 500:1, 1000:1, 2000:1, 5000:1, or 10000:1.

Another aspect of the present invention pertains to methods of treating a JAK3-associated disease or disorder in an individual (e.g., patient) by administering to the individual a therapeutically effective amount or dose of a compound of the present invention or a pharmaceutical composition thereof. In some embodiments, the individual has been diagnosed to have a JAK3-associated disease or disorder and is in need of treatment for the disease or disorder. A JAK3-associated disease can include any disease, disorder, or condition that is directly or indirectly linked to expression or activity of the JAK3, including over expression and/or abnormal activity levels. A JAK3-associated disease can also include any disease, disorder or condition that can be prevented, ameliorated, or cured by modulating JAK activity.

Examples of JAK3-associated diseases include diseases involving the immune system including, for example, organ transplant rejection [e.g., allograft rejection and graft versus host disease (GVHD)]. Some other examples of JAK3-associated diseases include a mast cell mediated immediate hypersensitivity reaction, platelet aggregation, and thrombus formation.

Further examples of JAK3-associated diseases include autoimmune diseases such as multiple sclerosis, rheumatoid arthritis, juvenile arthritis, psoriatic arthritis, type I diabetes, lupus, psoriasis, inflammatory bowel disease (e.g., ulcerative colitis and Crohn's disease), ankylosing spondylitis, myasthenia gravis, immunoglobulin nephropathies, autoimmune thyroid disorders, and the like. In some embodiments, the autoimmune disease is an autoimmune bullous skin disorder such as pemphigus vulgaris (PV) or bullous pemphigoid (BP). In some embodiments, JAK-associated diseases include rheumatoid arthritis.

Further examples of JAK3-associated diseases include allergic or type I hypersensitivity reaction such as urticaria and eczema, conjunctivitis, rhinorrhea, rhinitis, asthma, gastroenteritis, familial amyotrophic lateral sclerosis, lupus, multiple sclerosis, Type I diabetes and complications from diabetes, cancer, asthma, rhinitis, atopic dermatitis, autoimmune thyroid disorders, Alzheimer's disease, leukemia, thrombus and other autoimmune disease.

Further examples of JAK3-associated diseases or conditions include skin disorders such as vitiligo (e.g. trichrome vitiligo, marginal inflammatory vitiligo, quadrichrome vitiligo, blue vitiligo, Koebner phenomenon, localized vitiligo, including focal, segmental or mucosal subtypes, generalized vitiligo, including acrofacial, vulgaris or mixed subtypes, or universal vitiligo), psoriasis (for example, psoriasis vulgaris), atopic dermatitis, alopecia areata, patchy alopecia areata, alopecia totalis, alopecia universalis, ophiasis pattern alopecia areata, sisaihpo pattern alopecia areata, androgenetic alopecia (male and female pattern hair loss), telogen effluvium, hypotrichosis, hereditary hypotrichosis simplex, scarring alopecia, lichen planopilaris, central centrifugal cicatricial alopecia, skin rash, skin irritation, skin sensitization (e.g., contact dermatitis or allergic contact dermatitis). In some embodiments, the vitiligo may be selected from localized vitiligo, focal vitiligo, generalized vitiligo, segmental vitiligo, acral vitiligo, facial vitiligo, acrofacial vitiligo, mucosal vitiligo, confetti vitiligo, trichrome vitiligo, marginal inflammatory vitiligo, quadrichrome vitiligo, blue vitiligo, Koebner phenomenon, vulgaris vitiligo, mixed acrofacial, vulgaris vitiligo, or universal vitiligo. In some embodiments, the alopecia areata may be selected from patchy alopecia areata, alopecia totalis, alopecia universalis, ophiasis pattern alopecia areata, or sisaihpo pattern alopecia areata. For example, certain substances including some pharmaceuticals when topically applied can cause skin sensitization. In some embodiments, co-administration or sequential administration of at least one JAK3 inhibitor together with the agent causing unwanted sensitization can be helpful in treating such unwanted sensitization or dermatitis. In some embodiments, the skin disorder is treated by topical administration of at least one JAK inhibitor.

The JAK3 antagonists/inhibitors described herein can be used to treat any of the JAK3-associated diseases, disorders or conditions, or any combination thereof.

Treatment of the diseases/disorders herein includes treating one or more symptoms associated with the diseases/disorders. For example, symptoms of a JAK3-associated skin disorder (such as alopecia areata, vitiligo, psoriasis, atopic dermatitis, androgenetic alopecia (male or female pattern hair loss), skin rash, skin irritation, or skin sensitization) include itching (pruritus).

In some embodiments, the JAK3-associated condition, disease, or disorder may be a hair loss disorder. In some embodiments, the hair loss disorder may be selected from alopecia areata (including patchy alopecia areata, alopecia universalis, alopecia totalis, ophiasis pattern alopecia areata, and sisaihpo pattern alopecia areata), androgenetic alopecia (male and female pattern hair loss), lichen planopilaris, central centrifugal cicatricial alopecia, telogen effluvium, tinea capitis, hypotrichosis, hereditary hypotrichosis simplex, or the like.

As used herein, the term "contacting" refers to the bringing together of indicated moieties in an in vitro system or an in vivo system. For example, "contacting" a JAK3 with a JAK3 inhibitor compound includes the administration of a compound of the present invention to an individual or patient, such as a human, having a JAK3, as well as, for example, introducing a JAK3 inhibitor compound into a sample containing a cellular or purified preparation containing the JAK3.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician. The specific dose of a compound administered according to embodiments disclosed herein to obtain therapeutic and/or prophylactic effects will, of course, be determined by the particular circumstances surrounding the case, including, for example, the compound administered, the route of administration, and the condition being treated. The compounds are effective over a wide dosage range and it will be understood that the effective amount administered will be determined by the physician in the light of the relevant circumstances including the condition to be treated, the choice of compound to be administered, and the chosen route of administration. A therapeutically effective amount of compound of embodiments herein is typically an amount such that when it is administered in a physiologically tolerable excipient composition, it is sufficient to achieve an effective systemic concentration or local concentration in the tissue.

As used herein, the term "treating" or "treatment" refers to one or more of (1) preventing the disease; for example, preventing a disease, condition or disorder in an individual who may be predisposed to the disease, condition or disorder but does not yet experience or display the pathology or symptomatology of the disease; (2) inhibiting/retarding the disease; for example, inhibiting/retarding a disease, condition or disorder in an individual who is experiencing or displaying the pathology or symptomatology of the disease, condition or disorder; and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease or completely eliminating/curing the disease. As used herein, treating a disease further includes treating one or more symptoms associated with the disease.

Combination Therapies

One or more additional pharmaceutical agents such as, for example, anti-inflammatory agents, steroids, immunosuppressants, as well as one or more other JAK3 kinase inhibitors and/or other kinase inhibitors, such as BTK kinase, JAK1 kinase, JAK1/2 kinase, or JAK2 kinase inhibitors, such as, for example, those described in WO 99/65909, WO 00/00202, and/or WO/2004/099205, or other agents can be used in combination with the compounds of the present invention for treatment of JAK3-associated diseases, disorders or conditions. The one or more additional pharmaceutical agents can be administered to a patient simultaneously or sequentially.

In some embodiments, one or more JAK3 inhibitors/antagonists of embodiments herein can be used in combination with one or more other therapeutics used in the treatment of JAK3-mediated/associated conditions/diseases/disorders, and may improve the treatment response as compared to the response to the other therapeutics alone, without exacerbation of its toxic effects. In some embodiments, one or more JAK3 inhibitors/antagonists of embodiments herein can be used in combination with one or more other JAK3 inhibitors/antagonists for the treatment of JAK3-mediated/associated conditions/diseases/disorders. In some embodiments, one or more JAK3 inhibitors/antagonists can be used in combination with one or more JAK1 inhibitors/antagonists for the treatment of JAK3-mediated/associated conditions/diseases/disorders. In some embodiments, one or more JAK3 inhibitors/antagonists of embodiments herein can be used in combination with one or more JAK2 inhibitors/antagonists for the treatment of JAK3-mediated/associated conditions/diseases/disorders. In some embodiments, one or more JAK3 inhibitors/antagonists of embodiments herein can be used in combination with one or more "pan JAK" (JAK1/JAK2/JAK3) inhibitors/antagonists for the treatment of JAK3-mediated/associated conditions/diseases/disorders. In some embodiments, one or more JAK3 inhibitors/antagonists of embodiments herein can be used in combination with one or more TYK2 inhibitors/antagonists for the treatment of JAK3-mediated/associated conditions/diseases/disorders. In some embodiments, one or more JAK3 inhibitors/antagonists of embodiments herein can be used in combination with one or more JAK1/2 inhibitors/antagonists for the treatment of JAK3-mediated/associated conditions/diseases/disorders. Additive or synergistic effects are desirable outcomes of combining a JAK3 inhibitor/antagonist of embodiments herein with one or more additional agent. The additional agents can be combined with the present compounds in a single or continuous dosage form, or the agents can be administered simultaneously or sequentially as separate dosage forms. In some embodiments, one or more additional agents can be administered to a patient in combination with at least one JAK3 inhibitor/antagonist described herein where the additional agents are administered intermittently as opposed to continuously.

For example, in certain embodiments, a topically or orally administered JAK3 inhibitor/antagonist described herein can be used for the treatment of alopecia areata (patchy alopecia areata, alopecia totalis, alopecia universalis) alone or in combination with topical or intralesional corticosteroids, topical minoxidil, oral finasteride, oral dutasteride, contact sensitization therapy such as with squaric acid dibutyl ester, dinitrochlorobenzene, diphencyprone, topical or oral methoxalen and ultraviolet a (PUVA), topical anthralin, or laser therapy with e.g. the 308 nm xenon chloride excimer laser, hair transplantation procedures, or other therapies known to have beneficial effects in the condition.

In certain embodiments, a topically or orally administered JAK 3 inhibitor/antagonist disclosed herein can be used for the treatment of male or female-pattern baldness (androgenetic alopecia) alone or in combination with topical minoxidil, oral finasteride, oral dutasteride, topical antiandrogens, hair transplantation procedures, or other therapies known to have beneficial effects in the condition.

In certain embodiments, a topically or orally administered JAK 3 inhibitor/antagonist can be used for the treatment of vitiligo (e.g. localized vitiligo, focal vitiligo, generalized vitiligo, segmental vitiligo, acral vitiligo, facial vitiligo, acrofacial vitiligo, mucosal vitiligo, confetti vitiligo, trichrome vitiligo, marginal inflammatory vitiligo, quadrichrome vitiligo, blue vitiligo, Koebner phenomenon, vulgaris vitiligo, mixed acrofacial and vulgaris vitiligo, or universal vitiligo) alone or in combination with topical corticosteroids, topical tacrolimus, topical pimecrolimus, phototherapy such as ultraviolet light therapy with UVB, narrow-band UVB, oral or topical psoralen plus ultraviolet A (PUVA), calcipotriene or other topical vitamin D analogs, excimer laser phototherapy, systemic immunosuppressive agents, surgical treatments such as skin minigrafting, transplantation of autologous epidermal suspension, camouflage such as with make-up or dihydroxyacetone and such, or other therapies known to have beneficial effects in the condition.

Pharmaceutical Compositions and Dosage Forms

When employed as pharmaceuticals, the JAK3 inhibitor compounds can be administered in the form of pharmaceutical compositions. These compositions can be prepared in a manner well known in the pharmaceutical arts, and can be administered by a variety of routes, depending upon whether local or systemic treatment is desired and upon the area to be treated. Administration of the disclosed compounds or compositions may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions for topical administration may include foams, transdermal patches, ointments, lotions, creams, gels, solutions, fluid emulsions, fluid suspensions, semi-solids, pastes, drops, suppositories, sprays, liquids and powders. Conventional pharmaceutical carriers, aqueous, powder or oily bases, thickeners and the like may be necessary or desirable. Coated condoms, gloves and the like may also be useful. In some embodiments, the disclosed JAK3 inhibitor compounds can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The artisan can refer to various pharmacologic references for guidance. For example, *Modern Pharmaceutics*, 4$^{th}$ Edition, Banker & Rhodes, CRC Press (2002); and *Goodman & Gilman's The Pharmaceutical Basis of Therapeutics,* 12th Edition, McGraw Hill, New York (2011) can be consulted. In some embodiments, a method of treating a JAK3 associated disorder, disease or condition comprises administering a topical pharmaceutical composition of embodiments disclosed herein. In some embodiments, the topical pharmaceutical composition comprises JAK3 inhibitor/antagonist compound of embodiments herein. In some embodiments, the JAK3 inhibitor/antagonist compound is in a therapeutically effective amount. In some embodiments, the therapeutically effective amount is an amount disclosed herein.

Some embodiments disclosed herein also include pharmaceutical compositions which contain, as the active ingredient, one or more of the JAK3 inhibitor compounds above in combination with one or more pharmaceutically acceptable carriers (excipients).

In some embodiments, a method of making a pharmaceutical composition comprises, mixing the active ingredient with an excipient, diluting the active ingredient using an excipient, or enclosing the active ingredient within a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The JAK3 inhibitor compounds may be milled using known milling procedures such as wet milling to obtain a particle size appropriate for tablet formation and for other formulation types. Finely divided (nanoparticulate) preparations of the JAK3 inhibitor compounds can be prepared by processes known in the art, for example see International Patent Application No. WO 2002/000196, which is incorporated herein in its entirety.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions can be formulated so as to provide quick, sustained or delayed release of the active ingredient after administration to the patient by employing procedures known in the art.

The compositions can be formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and can be generally administered in a therapeutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

In some embodiments, the pharmaceutical composition may comprise about 0.01% to about 50% of one or more JAK3 inhibitor compounds disclosed herein. In some embodiments, the one or more JAK3 inhibitor compounds is in an amount of about 0.01% to about 50%, about 0.01% to about 45%, about 0.01% to about 40%, about 0.01% to about 30%, about 0.01% to about 20%, about 0.01% to about 10%, about 0.01% to about 5%, about 0.05% to about 50%, about 0.05% to about 45%, about 0.05% to about 40%, about 0.05% to about 30%, about 0.05% to about 20%, about 0.05% to about 10%, about 0.1% to about 50%, about 0.1% to about 45%, about 0.1% to about 40%, about 0.1% to about 30%, about 0.1% to about 20%, about 0.1% to about 10%, about 0.1% to about 5%, about 0.5% to about 50%, about 0.5% to about 45%, about 0.5% to about 40%, about 0.5% to about 30%, about 0.5% to about 20%, about 0.5% to about 10%, about 0.5% to about 5%, about 1% to about 50%, about 1% to about 45%, about 1% to about 40%, about 1% to about 35%, about 1% to about 30%, about 1% to about 25%, about 1% to about 20%, about 1% to about 15%, about 1% to about 10%, about 1% to about 5%, about 5% to about 45%, about 5% to about 40%, about 5% to about 35%, about 5% to about 30%, about 5% to about 25%, about 5% to about 20%, about 5% to about 15%, about 5% to about 10%, about 10% to about 45%, about 10% to about 40%, about 10% to about 35%, about 10% to about 30%, about 10% to about 25%, about 10% to about 20%, about 10% to about 15%, or a value within one of these ranges. Specific examples may include about 0.01%, about 0.05%, about 0.1%, about 0.25%, about 0.5%, about 0.75%, about 1%, about 5%, about 10%, about 15%, about 20%, about 25%, about 30%, about 35%, about 40%, about 45%, about 50%, about 60%, about 70%, about 80%, about 90%, or a range between any two of these values. In some embodiments, the composition is suited for topical administration.

In some embodiments, the JAK3 inhibitor compound is in a therapeutically effective amount. In some embodiments, the therapeutically effective amount may be about 1 mg to about 1000 mg, about 1 mg to about 900 mg, about 1 mg to about 800 mg, about 1 mg to about 700 mg, about 1 mg to about 600 mg, about 1 mg to about 500 mg, about 1 mg to about 400 mg, about 1 mg to about 300 mg, about 1 mg to about 200 mg, about 1 mg to about 100 mg, about 10 mg to about 1000 mg, about 50 mg to about 1000 mg, about 100 mg to about 1000 mg, about 200 mg to about 1000 mg, about 300 mg to about 1000 mg, about 400 mg to about 1000 mg, about 500 mg to about 1000 mg, about 10 mg to about 500 mg, about 50 mg to about 500 mg, about 100 mg to about 500 mg, about 10 mg to about 300 mg, about 50 mg to about 300 mg, from about 100 mg to about 300 mg, about 10 mg to about 150 mg, about 50 mg to about 150 mg, about 60 mg to about 120 mg, about 50 mg to about 120 mg or a range between any two of these values. Specific examples include, for example, about 1000 mg, about 900 mg, about 800 mg, about 700 mg, about 750 mg, about 600 mg, about 500 mg, about 400 mg, about 450 mg, about 300 mg, about 250 mg, about 200 mg, about 175 mg, about 150 mg, about 125 mg, about 120 mg, about 110 mg, about 100 mg, about 90 mg, about 80 mg, about 70 mg, about 60 mg, about 50 mg, about 30 mg, about 20 mg, or any value between the ranges disclosed above.

In some embodiments, the therapeutically effective amount can vary according to, for example, the particular use for which the treatment is made, the manner of administration of the compound, the health and condition of the patient, and the judgment of the prescribing physician. The proportion or concentration of a JAK3 inhibitor compound in a pharmaceutical composition can vary depending upon a number of factors including dosage, chemical characteristics (e.g., hydrophobicity), and the route of administration. For example, the JAK3 inhibitor compounds can be provided in an aqueous physiological buffer solution containing about 0.1 to about 10% w/v of the compound for parenteral administration. Some typical dose ranges for the JAK3 inhibitor compounds are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications.

For preparing solid compositions such as tablets, the principal active ingredient can be mixed with a pharmaceutical excipient to form a solid pre-formulation composition containing a homogeneous mixture of a compound of the present invention. When referring to these pre-formulation compositions as homogeneous, the active ingredient is typically dispersed evenly throughout the composition so that the composition can be readily subdivided into equally therapeutically effective unit dosage forms such as tablets, pills and capsules. This solid pre-formulation is then subdivided into unit dosage forms of the type described above containing from, for example, about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

In some embodiments, the compositions administered to a patient can be in the form of pharmaceutical compositions described above. In some embodiments, these compositions can be sterilized by conventional sterilization techniques, or may be sterile filtered. Aqueous solutions can be packaged for use as is, or lyophilized, the lyophilized preparation being combined with a sterile aqueous carrier prior to administration. In some embodiments, the pH of the compound preparations is about 3 to about 11, about 5 to about 9, about 5.5 to about 6.5, or about 5.5 to about 7.5. It will be understood that use of certain of the foregoing excipients, carriers, or stabilizers will result in the formation of pharmaceutical salts.

The compositions can further include one or more additional pharmaceutical agents such as a chemotherapeutic, steroid, anti-inflammatory compound, or immunosuppressant, examples of which are listed hereinabove.

Labeled Compounds and Assay Methods

Another aspect of the present invention relates to labeled JAK3 inhibitor compounds (radio-labeled, fluorescent-labeled, etc.) that would be useful not only in radio-imaging but also in assays, both in vitro and in vivo, for localizing and quantitating the enzyme in tissue samples, including human, and for identifying ligands by inhibition binding of a labeled compound. Accordingly, the present invention includes enzyme assays that contain such labeled compounds.

In some embodiments, the present invention further includes isotopically-labeled JAK3 inhibitor compounds. An "isotopically" or "radio-labeled" compound is a JAK3 inhibitor compound where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^{2}H$ (also written as D for deuterium), $^{3}H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. The radionuclide that is incorporated in the radio-labeled compounds will depend on the specific application of that radio-labeled compound. For example, for in vitro receptor labeling and competition assays, compounds that incorporate $^3$H, $^{14}$C, $^{82}$Br, $^{125}$I, $^{131}$I, $^{35}$S or will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

It is understood that a "radio-labeled compound" is a compound that has incorporated at least one radionuclide. In some embodiments the radionuclide is selected from $^3$H, $^{14}$C, $^{125}$I, $^{35}$S and $^{82}$Br.

In some embodiments, the labeled compounds contain a fluorescent label.

Synthetic methods for incorporating radio-isotopes and fluorescent labels into organic compounds are well known in the art.

A labeled JAK3 inhibitor compound (radio-labeled, fluorescent-labeled, etc.) can be used in a screening assay to identify/evaluate compounds. For example, a newly synthesized or identified compound (i.e., test compound) which is labeled can be evaluated for its ability to bind a JAK3 by monitoring its concentration variation when contacting with the JAK3, through tracking the labeling. For another example, a test compound (labeled) can be evaluated for its ability to reduce binding of another compound which is known to bind to JAK3 (i.e., standard compound). Accordingly, the ability of a test compound to compete with the standard compound for binding to the JAK3 directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

In some embodiments, the present invention also includes pharmaceutical kits useful, for example, in the treatment or prevention of JAK3-associated diseases or disorders such as vitiligo, localized vitiligo, focal vitiligo, generalized vitiligo, segmental vitiligo, acral vitiligo, facial vitiligo, acrofacial vitiligo, mucosal vitiligo, confetti vitiligo, trichrome vitiligo, marginal inflammatory vitiligo, quadrichrome vitiligo, blue vitiligo, Koebner phenomenon, vulgaris vitiligo, mixed acrofacial and vulgaris vitiligo, universal vitiligo, psoriasis, psoriasis vulgaris, atopic dermatitis, alopecia areata, patchy alopecia areata, alopecia totalis, alopecia universalis, ophiasis pattern alopecia areata, sisaihpo pattern alopecia areata, androgenetic alopecia (male and female pattern hair loss), telogen effluvium, hypotrichosis, hereditary hypotrichosis simplex, scarring alopecia, lichen planopilaris, central centrifugal cicatricial alopecia, skin rash, skin irritation, skin sensitization, contact dermatitis, or allergic contact dermatitis, allergies, asthma, autoimmune diseases such as transplant rejection, rheumatoid arthritis, amyotrophic lateral sclerosis and multiple sclerosis as well as in solid and hematologic malignancies such as leukemias and lymphomas, and other diseases referred to herein which include one or more containers containing a pharmaceutical composition comprising a therapeutically effective amount of a JAK3 inhibitor compound. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

In some instances where the compounds disclosed herein were isolated by preparative HPLC in the presence of trifluoroacetic acid (TFA) or other acid, the compounds of embodiments herein may have been obtained as the corresponding salt. The disclosed compounds were found to be inhibitors of JAK3 according to one or more of the assays provided herein. In some embodiments, the $IC_{50}$ value for the compound with respect JAK3 is less than about 100, 80, 50, 20, 10, 8, 5, 2, or 1 µM. In some embodiments, the $IC_{50}$ value for the compounds of embodiments herein with respect to JAK3 is less than about 1000, 800, 500, 200, 100, 80, 50, 20, 10, 5, 2, or 1 nM. Certain compounds described in Table 1 and in the Example section were tested for inhibitory activity of JAK3 targets according to assays such as those described herein or those known in the art (e.g., Ma H et al, Expert Opin. Drug Discov. 3, 607-621 (2008); Olive D M, Expert Rev Proteomics, 1, 327-341 (2004)). Some embodiments will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results.

Example 1: Hair Growth Induction Model

Figure 2:
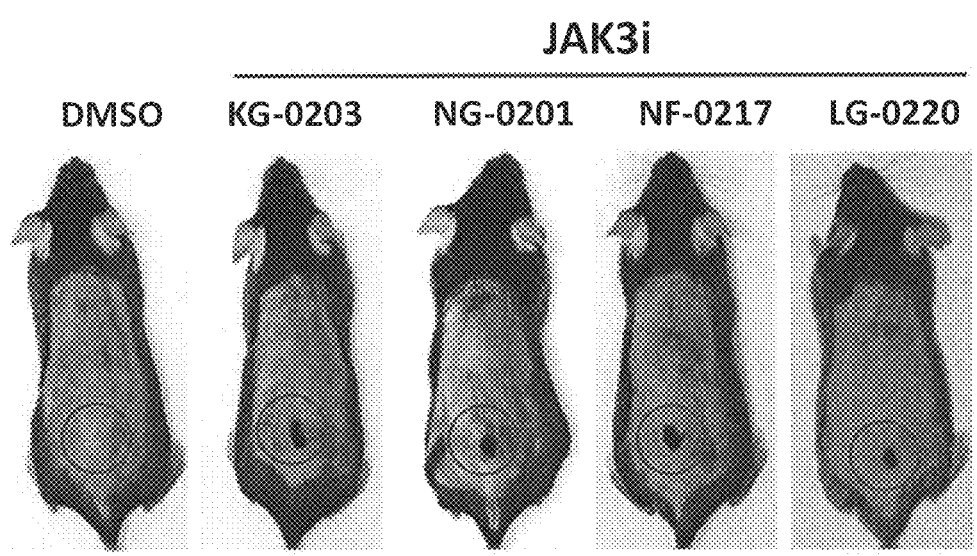
FIG. 2 illustrates that covalent JAK3i promotes hair growth (AGA model) in seven-wk-old C57BL/6 mice.

The anagen induction model was used in telogen mouse skin to test the ability of JAK3 inhibitors to induce the hair cycle. Each pair of approximately eight-week-old C57BL/6 mice were shaved and treated with 30 ul 2% of the four different Jak3 inhibitors or DMSO alone (as vehicle) by daily application on the lower dorsal back for 10 days (FIG. 2). Darkening of the skin was observed after approximately 14-18 days with eruption of new anagen hairs at approximately 28 days.

Example 2: AA Prevention Model

Figure 3:
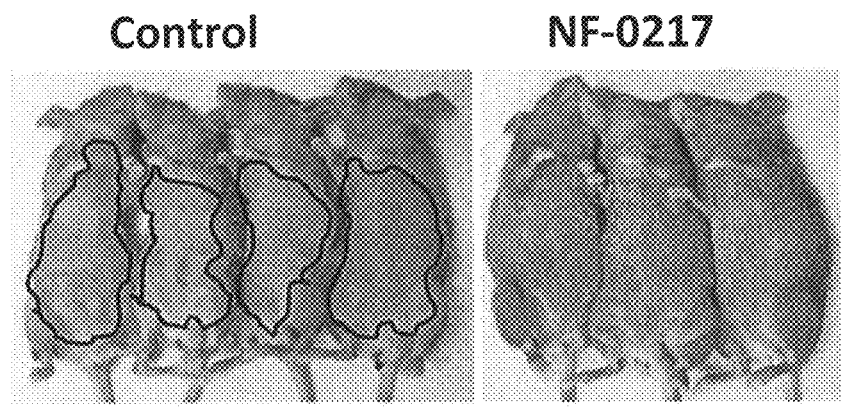
FIG. 3 illustrates that covalent JAK3i prevents the development of AA in NF-0217 mice.

For prevention of AA in the graft model, a cohort of seven C3H/HeJ mice were grafted with skin from an AA-affected mouse in the second telogen of recipients, at approximately 7 weeks of age. Grafted mice were given treatment beginning the day of grafting. The Jak3 inhibitor NF-0217 or control was administered by i.p. injection (0.5 mg in 50 µl Ploy (ethylene glycol) daily for 8 weeks (FIG. 3). After 6 weeks, the four control-treated mice lost their hair as expected in the AA model. In contrast, the three JAK3i treated mice all retained their hair.

Various modifications, in addition to those described herein, will be apparent to those skilled in the art from the foregoing description. Such modifications are also intended to fall within the scope of the appended claims. Each reference cited in the present application is herein incorporated by reference in its entirety.

What is claimed is:

1. A JAK3 inhibitor compound selected from:

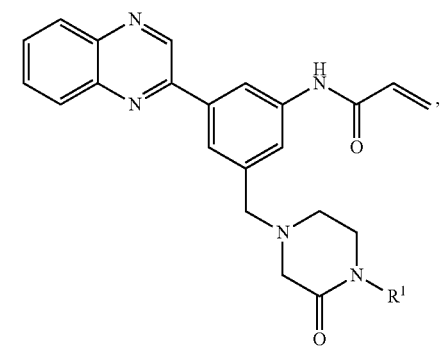

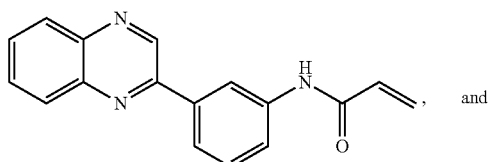 and

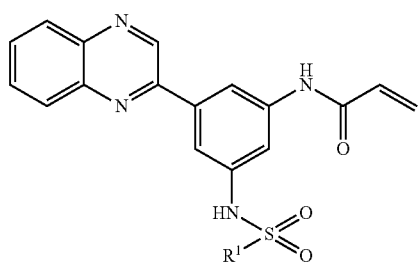

wherein $R^1$ is H or $C_1$-$C_6$ alkyl;
or a pharmaceutically acceptable salt thereof.

2. The compound of claim 1, wherein the JAK3 inhibitor compound is

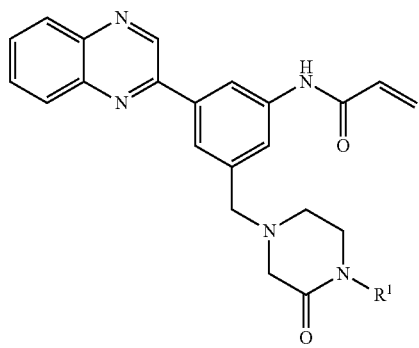

wherein $R^1$ is H or $C_1$-$C_6$ alkyl;
or a pharmaceutically acceptable salt thereof.

3. The compound of claim 1, wherein the JAK3 inhibitor compound is

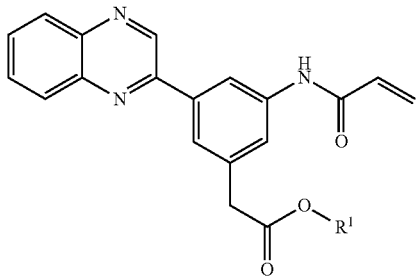

wherein $R^1$ is H or $C_1$-$C_6$ alkyl;
or a pharmaceutically acceptable salt thereof.

4. The compound of claim 1, wherein the JAK3 inhibitor compound is

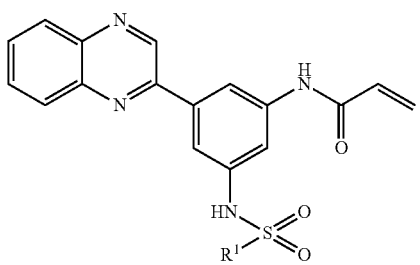

wherein $R^1$ is H or $C_1$-$C_6$ alkyl;
or a pharmaceutically acceptable salt thereof.

5. The compound of claim 1, wherein the JAK3 inhibitor compound is a compound of formula 1a:

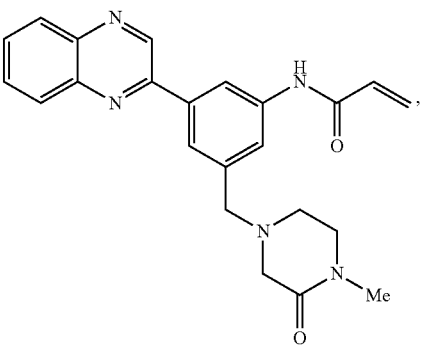 [SMILES: C=CC(=O)Nc1cc(CN2CCN(C)C(=O)C2)cc(-c2cnc3ccccc3n2)c1]

or a pharmaceutically acceptable salt thereof.

6. The compound of claim 1, wherein the JAK3 inhibitor compound is a compound of formula 1b:

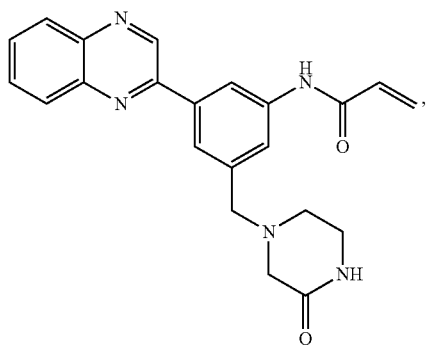
or a pharmaceutically acceptable salt thereof.
\* \* \* \* \*